US009079000B2

(12) United States Patent
Hanson et al.

(10) Patent No.: US 9,079,000 B2
(45) Date of Patent: Jul. 14, 2015

(54) INTEGRATED CROSSING BALLOON CATHETER

(71) Applicant: BOSTON SCIENTIFIC SCIMED, INC., Maple Grove, MN (US)

(72) Inventors: Cass A. Hanson, St. Paul, MN (US); Barry E. Rudman, Forest Lake, MN (US); Ajay Gupta, Little Canada, MN (US); Daniel T. Quillin, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 175 days.

(21) Appl. No.: 13/653,114

(22) Filed: Oct. 16, 2012

(65) Prior Publication Data

US 2013/0096604 A1    Apr. 18, 2013

Related U.S. Application Data

(60) Provisional application No. 61/548,629, filed on Oct. 18, 2011.

(51) Int. Cl.
*A61M 29/02*    (2006.01)
*A61M 25/10*    (2013.01)
(Continued)

(52) U.S. Cl.
CPC .... *A61M 25/104* (2013.01); *A61B 2017/22044* (2013.01); *A61B 2017/22094* (2013.01);
(Continued)

(58) Field of Classification Search
CPC ................... A61M 25/104; A61M 2025/0024; A61M 29/02; A61F 22/9583; A61F 2/962

USPC ....................... 606/153; 604/103.05
See application file for complete search history.

(56) References Cited

U.S. PATENT DOCUMENTS

| 164,184 A | 6/1875 | Kidder |
| 1,167,014 A | 1/1916 | O'Brien |

(Continued)

FOREIGN PATENT DOCUMENTS

| DE | 10038737 A1 | 2/2002 |
| EP | 0405831 B1 | 6/1995 |

(Continued)

OTHER PUBLICATIONS

Terumo Corporation Press Release, "New Release of Terumo PTCA Catehter RX-2 (pet name "Ryujin Plus"), a Device for Use in the Treatment of Angina and Myocardial Infarction," Jan. 7, 2005, 2 sheets.

(Continued)

*Primary Examiner* — Jonathan W Miles
*Assistant Examiner* — George J Ulsh
(74) *Attorney, Agent, or Firm* — Seager, Tufte & Wickhem, LLC

(57) ABSTRACT

An integrated crossing balloon catheter. The catheter includes a hub assembly secured to the proximal end of the catheter shaft, an inflatable balloon secured to the distal end of the catheter shaft, and a stiffening tube positioned over the inflatable balloon and a distal end portion of the catheter shaft. The stiffening tube is configured to be advanced through a vasculature with the catheter shaft as a unit. The stiffening tube is translatable along the catheter shaft from a first position in which the inflatable balloon is within the stiffening tube to a second position in which the inflatable balloon is exposed from the stiffening tube.

18 Claims, 11 Drawing Sheets

(51) Int. Cl.
*A61F 2/958* (2013.01)
*A61M 25/00* (2006.01)
*A61B 17/22* (2006.01)

(52) U.S. Cl.
CPC . *A61F2002/9583* (2013.01); *A61M 2025/0024* (2013.01); *A61M 2025/1061* (2013.01); *A61M 2025/1081* (2013.01)

(56) References Cited

U.S. PATENT DOCUMENTS

| | | |
|---|---|---|
| 2,505,358 A | 4/1950 | Gusberg et al. |
| 2,701,559 A | 2/1955 | Cooper |
| 3,108,593 A | 10/1963 | Glassman |
| 3,108,594 A | 10/1963 | Glassman |
| 3,540,431 A | 11/1970 | Mobin |
| 3,952,747 A | 4/1976 | Kimmell |
| 3,996,938 A | 12/1976 | Clark, III |
| 4,046,150 A | 9/1977 | Schwartz et al. |
| 4,093,484 A | 6/1978 | Harrison et al. |
| 4,137,906 A | 2/1979 | Akiyama et al. |
| 4,290,427 A | 9/1981 | Chin |
| 4,402,686 A | 9/1983 | Medel |
| 4,483,341 A | 11/1984 | Witteles et al. |
| 4,574,804 A | 3/1986 | Kurwa |
| 4,582,181 A | 4/1986 | Samson |
| 4,585,000 A * | 4/1986 | Hershenson ............... 606/194 |
| 4,587,975 A | 5/1986 | Salo et al. |
| 4,649,936 A | 3/1987 | Ungar et al. |
| 4,682,596 A | 7/1987 | Bales et al. |
| 4,709,698 A | 12/1987 | Johnston et al. |
| 4,748,982 A | 6/1988 | Horzewski et al. |
| 4,762,129 A | 8/1988 | Bonzel |
| 4,765,331 A | 8/1988 | Petruzzi et al. |
| 4,770,653 A | 9/1988 | Shturman |
| 4,771,777 A | 9/1988 | Horzewski et al. |
| 4,784,132 A | 11/1988 | Fox et al. |
| 4,784,162 A | 11/1988 | Ricks et al. |
| 4,785,806 A | 11/1988 | Deckelbaum et al. |
| 4,788,975 A | 12/1988 | Shturman et al. |
| 4,790,310 A | 12/1988 | Ginsburg et al. |
| 4,799,479 A | 1/1989 | Spears |
| 4,819,751 A | 4/1989 | Shimada et al. |
| 4,823,791 A | 4/1989 | D'Amelio et al. |
| 4,830,003 A | 5/1989 | Wolff et al. |
| 4,849,484 A | 7/1989 | Heard |
| 4,862,886 A | 9/1989 | Clarke et al. |
| 4,887,605 A | 12/1989 | Angelsen et al. |
| 4,906,241 A | 3/1990 | Noddin et al. |
| 4,917,088 A | 4/1990 | Crittendon |
| 4,917,103 A | 4/1990 | Gambale et al. |
| 4,917,666 A | 4/1990 | Solar et al. |
| 4,920,979 A | 5/1990 | Bullara et al. |
| 4,922,923 A | 5/1990 | Gambale et al. |
| 4,938,766 A | 7/1990 | Jarvik |
| 4,943,278 A | 7/1990 | Euteneuer et al. |
| 4,955,377 A | 9/1990 | Lennox et al. |
| 4,955,895 A | 9/1990 | Sugiyama et al. |
| 4,964,409 A | 10/1990 | Tremulis |
| 4,976,711 A | 12/1990 | Parins et al. |
| 4,988,356 A | 1/1991 | Crittenden et al. |
| 4,998,917 A | 3/1991 | Gaiser et al. |
| 4,998,923 A | 3/1991 | Samson et al. |
| 5,002,532 A | 3/1991 | Gaiser et al. |
| 5,019,042 A | 5/1991 | Sahota |
| 5,034,010 A | 7/1991 | Kittrell et al. |
| 5,040,548 A | 8/1991 | Yock |
| 5,042,985 A | 8/1991 | Elliott et al. |
| 5,052,402 A | 10/1991 | Bencini et al. |
| 5,053,033 A | 10/1991 | Clarke et al. |
| 5,061,273 A | 10/1991 | Yock |
| 5,071,424 A | 12/1991 | Reger et al. |
| 5,074,871 A | 12/1991 | Groshong et al. |
| 5,095,915 A | 3/1992 | Engelson |
| 5,098,429 A | 3/1992 | Sterzer et al. |
| 5,098,431 A | 3/1992 | Rydell |
| 5,109,859 A | 5/1992 | Jenkins |
| 5,125,928 A | 6/1992 | Parins et al. |
| 5,129,396 A | 7/1992 | Rosen et al. |
| 5,135,535 A | 8/1992 | Kramer et al. |
| 5,139,496 A | 8/1992 | Hed |
| 5,143,836 A | 9/1992 | Hartman et al. |
| 5,154,725 A | 10/1992 | Leopold |
| 5,156,594 A | 10/1992 | Keith |
| 5,156,610 A | 10/1992 | Reger et al. |
| 5,158,564 A | 10/1992 | Schnepp-Pesch |
| 5,170,802 A | 12/1992 | Mehra |
| 5,171,222 A | 12/1992 | Euteneuer et al. |
| 5,176,637 A | 1/1993 | Sagae |
| 5,178,620 A | 1/1993 | Eggers et al. |
| 5,178,625 A | 1/1993 | Groshong et al. |
| 5,180,367 A | 1/1993 | Kontos et al. |
| 5,190,540 A | 3/1993 | Lee |
| 5,209,728 A | 5/1993 | Kraus et al. |
| 5,211,651 A | 5/1993 | Reger et al. |
| 5,217,482 A | 6/1993 | Keith |
| 5,232,445 A | 8/1993 | Bonzel |
| 5,234,407 A | 8/1993 | Teirstein et al. |
| 5,238,004 A | 8/1993 | Sahatjian et al. |
| 5,242,396 A | 9/1993 | Evard |
| 5,242,441 A | 9/1993 | Avitall |
| 5,246,421 A * | 9/1993 | Saab ............................ 606/194 |
| 5,251,634 A | 10/1993 | Weinberg et al. |
| 5,255,679 A | 10/1993 | Imran |
| 5,263,493 A | 11/1993 | Avitall |
| 5,267,954 A | 12/1993 | Nita et al. |
| 5,267,958 A | 12/1993 | Buchbinder et al. |
| 5,277,199 A | 1/1994 | DuBois et al. |
| 5,277,201 A | 1/1994 | Stern et al. |
| 5,279,562 A | 1/1994 | Sirhan et al. |
| 5,282,484 A | 2/1994 | Reger et al. |
| 5,286,254 A | 2/1994 | Shapland et al. |
| 5,290,295 A | 3/1994 | Querals et al. |
| 5,295,484 A | 3/1994 | Marcus |
| 5,297,564 A | 3/1994 | Love et al. |
| 5,300,025 A | 4/1994 | Wantink |
| 5,300,068 A | 4/1994 | Rosar et al. |
| 5,300,085 A | 4/1994 | Yock |
| 5,301,683 A | 4/1994 | Durkan |
| 5,304,115 A | 4/1994 | Pflueger et al. |
| 5,304,121 A | 4/1994 | Sahatjian |
| 5,304,171 A | 4/1994 | Gregory et al. |
| 5,304,173 A | 4/1994 | Kittrell et al. |
| 5,306,247 A | 4/1994 | Pfenninger |
| 5,306,250 A | 4/1994 | March et al. |
| 5,312,328 A | 5/1994 | Nita et al. |
| 5,314,466 A | 5/1994 | Stern et al. |
| 5,322,064 A | 6/1994 | Lundquist |
| 5,322,505 A | 6/1994 | Krause et al. |
| 5,324,255 A | 6/1994 | Passafaro et al. |
| 5,324,269 A | 6/1994 | Miraki |
| 5,326,341 A | 7/1994 | Lew et al. |
| 5,326,342 A | 7/1994 | Pflueger et al. |
| 5,328,468 A | 7/1994 | Kaneko et al. |
| 5,328,472 A | 7/1994 | Steinke et al. |
| 5,330,518 A | 7/1994 | Neilson et al. |
| 5,333,614 A | 8/1994 | Feiring |
| 5,342,292 A | 8/1994 | Nita et al. |
| 5,344,395 A | 9/1994 | Whalen et al. |
| 5,346,505 A | 9/1994 | Leopold |
| 5,350,395 A | 9/1994 | Yock |
| 5,364,376 A | 11/1994 | Horzewski et al. |
| 5,364,392 A | 11/1994 | Warner et al. |
| 5,365,172 A | 11/1994 | Hrovat et al. |
| 5,368,557 A | 11/1994 | Nita et al. |
| 5,368,558 A | 11/1994 | Nita et al. |
| 5,370,616 A | 12/1994 | Keith et al. |
| 5,380,274 A | 1/1995 | Nita et al. |
| 5,380,319 A | 1/1995 | Saito et al. |
| 5,382,228 A | 1/1995 | Nita et al. |
| 5,382,234 A | 1/1995 | Cornelius et al. |
| 5,383,874 A | 1/1995 | Jackson et al. |
| 5,383,917 A | 1/1995 | Desai et al. |
| 5,387,193 A | 2/1995 | Miraki |

(56) References Cited

U.S. PATENT DOCUMENTS

| | | |
|---|---|---|
| 5,389,087 A | 2/1995 | Miraki |
| 5,395,334 A | 3/1995 | Keith et al. |
| 5,395,335 A | 3/1995 | Jang |
| 5,397,301 A | 3/1995 | Pflueger et al. |
| 5,397,339 A | 3/1995 | Desai |
| 5,401,272 A | 3/1995 | Perkins et al. |
| 5,403,311 A | 4/1995 | Abele et al. |
| 5,405,318 A | 4/1995 | Nita et al. |
| 5,405,346 A | 4/1995 | Grundy et al. |
| 5,409,000 A | 4/1995 | Imran |
| 5,410,797 A | 5/1995 | Steinke et al. |
| 5,413,559 A | 5/1995 | Sirhan et al. |
| 5,417,672 A | 5/1995 | Nita et al. |
| 5,419,767 A | 5/1995 | Eggers et al. |
| 5,423,754 A | 6/1995 | Cornelius et al. |
| 5,425,711 A | 6/1995 | Ressemann et al. |
| 5,427,118 A | 6/1995 | Nita et al. |
| 5,432,876 A | 7/1995 | Appeldorn et al. |
| 5,439,447 A | 8/1995 | Miraki |
| 5,441,498 A | 8/1995 | Perkins et al. |
| 5,447,509 A | 9/1995 | Mills et al. |
| 5,451,207 A | 9/1995 | Yock et al. |
| 5,451,233 A | 9/1995 | Yock |
| 5,453,091 A | 9/1995 | Taylor et al. |
| 5,454,788 A | 10/1995 | Walker et al. |
| 5,454,809 A | 10/1995 | Janssen |
| 5,455,029 A | 10/1995 | Hartman et al. |
| 5,456,680 A | 10/1995 | Taylor et al. |
| 5,456,682 A | 10/1995 | Edwards et al. |
| 5,457,042 A | 10/1995 | Hartman et al. |
| 5,458,613 A | 10/1995 | Gharibadeh et al. |
| 5,458,639 A | 10/1995 | Tsukashima et al. |
| 5,470,315 A | 11/1995 | Adams |
| 5,471,982 A | 12/1995 | Edwards et al. |
| 5,474,530 A | 12/1995 | Passafaro et al. |
| 5,477,856 A | 12/1995 | Lundquist |
| 5,478,351 A | 12/1995 | Meade et al. |
| 5,480,382 A | 1/1996 | Hammerslag et al. |
| 5,489,271 A | 2/1996 | Andersen |
| 5,490,837 A | 2/1996 | Blaeser et al. |
| 5,496,275 A | 3/1996 | Sirhan et al. |
| 5,496,294 A | 3/1996 | Hergenrother et al. |
| 5,496,311 A | 3/1996 | Abele et al. |
| 5,496,312 A | 3/1996 | Klicek et al. |
| 5,496,346 A | 3/1996 | Horzewski et al. |
| 5,498,261 A | 3/1996 | Strul |
| 5,505,201 A | 4/1996 | Grill et al. |
| 5,505,730 A | 4/1996 | Edwards |
| 5,507,301 A | 4/1996 | Wasicek et al. |
| 5,507,744 A | 4/1996 | Tay et al. |
| 5,507,751 A | 4/1996 | Goode et al. |
| 5,507,766 A | 4/1996 | Kugo et al. |
| 5,522,818 A | 6/1996 | Keith et al. |
| 5,522,873 A | 6/1996 | Jackman et al. |
| 5,531,520 A | 7/1996 | Grimson et al. |
| 5,531,690 A | 7/1996 | Solar |
| 5,540,656 A | 7/1996 | Pflueger et al. |
| 5,540,679 A | 7/1996 | Fram et al. |
| 5,540,681 A | 7/1996 | Strul et al. |
| 5,542,434 A | 8/1996 | Imran et al. |
| 5,542,917 A | 8/1996 | Nita et al. |
| 5,545,134 A | 8/1996 | Hilaire et al. |
| 5,545,138 A | 8/1996 | Fugoso et al. |
| 5,545,161 A | 8/1996 | Imran |
| 5,549,552 A | 8/1996 | Peters et al. |
| 5,549,557 A | 8/1996 | Steinke et al. |
| 5,562,100 A | 10/1996 | Kittrell et al. |
| 5,569,201 A | 10/1996 | Burns |
| 5,571,122 A | 11/1996 | Kelly et al. |
| 5,571,151 A | 11/1996 | Gregory |
| 5,573,531 A | 11/1996 | Gregory et al. |
| 5,573,533 A | 11/1996 | Strul |
| 5,584,831 A | 12/1996 | McKay |
| 5,584,872 A | 12/1996 | Lafontaine et al. |
| 5,588,962 A | 12/1996 | Nicholas et al. |
| 5,599,346 A | 2/1997 | Edwards et al. |
| 5,601,526 A | 2/1997 | Chapelon et al. |
| 5,605,543 A | 2/1997 | Swanson |
| 5,607,394 A | 3/1997 | Andersen et al. |
| 5,609,606 A | 3/1997 | O'Boyle et al. |
| 5,626,576 A | 5/1997 | Janssen |
| 5,626,593 A | 5/1997 | Imran |
| 5,626,600 A | 5/1997 | Horzewski et al. |
| 5,630,837 A | 5/1997 | Crowley |
| 5,634,902 A | 6/1997 | Johnson et al. |
| 5,637,090 A | 6/1997 | McGee et al. |
| 5,637,902 A | 6/1997 | Jiang |
| 5,643,255 A | 7/1997 | Organ |
| 5,643,297 A | 7/1997 | Nordgren et al. |
| 5,647,847 A | 7/1997 | Lafontaine et al. |
| 5,649,923 A | 7/1997 | Gregory et al. |
| 5,651,780 A | 7/1997 | Jackson et al. |
| 5,653,684 A | 8/1997 | Laptewicz et al. |
| 5,658,251 A | 8/1997 | Ressemann et al. |
| 5,662,671 A | 9/1997 | Barbut et al. |
| 5,665,062 A | 9/1997 | Houser |
| 5,665,098 A | 9/1997 | Kelly et al. |
| 5,666,964 A | 9/1997 | Meilus |
| 5,667,490 A | 9/1997 | Keith et al. |
| 5,667,493 A | 9/1997 | Janacek |
| 5,672,174 A | 9/1997 | Gough et al. |
| 5,676,693 A | 10/1997 | Lafontaine |
| 5,678,296 A | 10/1997 | Fleischhacker et al. |
| 5,681,282 A | 10/1997 | Eggers et al. |
| RE35,648 E | 11/1997 | Tenerz et al. |
| RE35,656 E | 11/1997 | Feinberg |
| 5,688,266 A | 11/1997 | Edwards et al. |
| 5,690,613 A | 11/1997 | Verbeek |
| 5,693,015 A | 12/1997 | Walker et al. |
| 5,693,029 A | 12/1997 | Leonhardt et al. |
| 5,693,043 A | 12/1997 | Kittrell et al. |
| 5,693,082 A | 12/1997 | Warner et al. |
| 5,695,504 A | 12/1997 | Gifford et al. |
| 5,697,369 A | 12/1997 | Long, Jr. et al. |
| 5,697,909 A | 12/1997 | Eggers et al. |
| 5,702,386 A | 12/1997 | Stern et al. |
| 5,702,433 A | 12/1997 | Taylor et al. |
| 5,702,439 A | 12/1997 | Keith et al. |
| 5,706,809 A | 1/1998 | Littmann et al. |
| 5,709,658 A | 1/1998 | Sirhan et al. |
| 5,713,942 A | 2/1998 | Stern et al. |
| 5,715,819 A | 2/1998 | Svenson et al. |
| 5,718,683 A | 2/1998 | Ressemann et al. |
| 5,720,724 A | 2/1998 | Ressemann et al. |
| 5,728,067 A | 3/1998 | Enger |
| 5,735,846 A | 4/1998 | Panescu et al. |
| 5,741,214 A | 4/1998 | Ouchi et al. |
| 5,741,248 A | 4/1998 | Stern et al. |
| 5,741,249 A | 4/1998 | Moss et al. |
| 5,743,876 A | 4/1998 | Swanson |
| 5,743,903 A | 4/1998 | Stern et al. |
| 5,748,347 A | 5/1998 | Erickson |
| 5,749,888 A | 5/1998 | Yock |
| 5,749,914 A | 5/1998 | Janssen |
| 5,755,682 A | 5/1998 | Knudson et al. |
| 5,755,715 A | 5/1998 | Stern et al. |
| 5,755,753 A | 5/1998 | Knowlton et al. |
| 5,769,847 A | 6/1998 | Panescu et al. |
| 5,769,868 A | 6/1998 | Yock |
| 5,769,880 A | 6/1998 | Truckai et al. |
| 5,772,609 A | 6/1998 | Nguyen et al. |
| 5,775,338 A | 7/1998 | Hastings |
| 5,776,100 A | 7/1998 | Forman |
| 5,776,174 A | 7/1998 | Van Tassel |
| 5,779,698 A | 7/1998 | Clayman et al. |
| 5,782,760 A | 7/1998 | Schaer |
| 5,785,702 A | 7/1998 | Murphy-Chutorian et al. |
| 5,797,849 A | 8/1998 | Vesely et al. |
| 5,797,903 A | 8/1998 | Swanson et al. |
| 5,800,484 A | 9/1998 | Gough et al. |
| 5,800,494 A | 9/1998 | Campbell et al. |
| 5,807,355 A | 9/1998 | Ramzipoor et al. |
| 5,810,802 A | 9/1998 | Panescu et al. |
| 5,810,803 A | 9/1998 | Moss et al. |

(56) References Cited

U.S. PATENT DOCUMENTS

| | | |
|---|---|---|
| 5,810,810 A | 9/1998 | Tay et al. |
| 5,810,867 A | 9/1998 | Zarbatany et al. |
| 5,810,869 A | 9/1998 | Kaplan et al. |
| 5,817,092 A | 10/1998 | Behl |
| 5,817,113 A | 10/1998 | Gifford et al. |
| 5,817,144 A | 10/1998 | Gregory et al. |
| 5,823,956 A | 10/1998 | Roth et al. |
| 5,823,995 A | 10/1998 | Fitzmaurice et al. |
| 5,827,203 A | 10/1998 | Nita et al. |
| 5,827,268 A | 10/1998 | Laufer |
| 5,829,447 A | 11/1998 | Stevens et al. |
| 5,830,213 A | 11/1998 | Panescu et al. |
| 5,830,222 A | 11/1998 | Makower |
| 5,832,228 A | 11/1998 | Holden et al. |
| 5,833,593 A | 11/1998 | Liprie |
| 5,833,706 A | 11/1998 | St. Germain et al. |
| 5,836,874 A | 11/1998 | Swanson et al. |
| 5,840,076 A | 11/1998 | Swanson et al. |
| 5,843,016 A | 12/1998 | Lugnani et al. |
| 5,846,238 A | 12/1998 | Jackson et al. |
| 5,846,239 A | 12/1998 | Swanson et al. |
| 5,846,245 A | 12/1998 | McCarthy et al. |
| 5,848,969 A | 12/1998 | Panescu et al. |
| 5,853,411 A | 12/1998 | Whayne et al. |
| 5,855,614 A | 1/1999 | Stevens et al. |
| 5,860,974 A | 1/1999 | Abele |
| 5,865,801 A | 2/1999 | Houser |
| 5,868,735 A | 2/1999 | Lafontaine et al. |
| 5,868,736 A | 2/1999 | Swanson et al. |
| 5,871,483 A | 2/1999 | Jackson et al. |
| 5,871,524 A | 2/1999 | Knowlton et al. |
| 5,875,782 A | 3/1999 | Ferrari et al. |
| 5,876,369 A | 3/1999 | Houser |
| 5,876,374 A | 3/1999 | Alba et al. |
| 5,876,375 A | 3/1999 | Penny |
| 5,876,397 A | 3/1999 | Edelman et al. |
| 5,879,348 A | 3/1999 | Owens et al. |
| 5,882,336 A | 3/1999 | Janacek |
| 5,891,114 A | 4/1999 | Chien et al. |
| 5,891,135 A | 4/1999 | Jackson et al. |
| 5,891,136 A | 4/1999 | McGee et al. |
| 5,891,138 A | 4/1999 | Tu et al. |
| 5,895,378 A | 4/1999 | Nita |
| 5,897,552 A | 4/1999 | Edwards et al. |
| 5,902,328 A | 5/1999 | Lafontaine et al. |
| 5,904,651 A | 5/1999 | Swanson et al. |
| 5,904,667 A | 5/1999 | Falwell et al. |
| 5,904,697 A | 5/1999 | Gifford et al. |
| 5,904,709 A | 5/1999 | Arndt et al. |
| 5,906,614 A | 5/1999 | Stern et al. |
| 5,906,623 A | 5/1999 | Peterson |
| 5,906,636 A | 5/1999 | Casscells et al. |
| 5,911,715 A | 6/1999 | Berg et al. |
| 5,916,192 A | 6/1999 | Nita et al. |
| 5,916,227 A | 6/1999 | Keith et al. |
| 5,916,239 A | 6/1999 | Geddes et al. |
| 5,919,219 A | 7/1999 | Knowlton et al. |
| 5,921,958 A | 7/1999 | Ressemann et al. |
| 5,921,971 A | 7/1999 | Agro et al. |
| 5,924,424 A | 7/1999 | Stevens et al. |
| 5,925,038 A | 7/1999 | Panescu et al. |
| 5,931,812 A | 8/1999 | Andersen et al. |
| 5,934,284 A | 8/1999 | Plaia et al. |
| 5,935,063 A | 8/1999 | Nguyen |
| 5,938,670 A | 8/1999 | Keith et al. |
| 5,947,977 A | 9/1999 | Slepian et al. |
| 5,948,011 A | 9/1999 | Knowlton et al. |
| 5,951,494 A | 9/1999 | Wang et al. |
| 5,951,539 A | 9/1999 | Nita et al. |
| 5,954,717 A | 9/1999 | Behl et al. |
| 5,957,882 A | 9/1999 | Nita et al. |
| 5,957,903 A | 9/1999 | Mirzaee et al. |
| 5,957,941 A | 9/1999 | Ream et al. |
| 5,957,969 A | 9/1999 | Warner et al. |
| 5,961,485 A | 10/1999 | Martin |
| 5,961,490 A | 10/1999 | Adams |
| 5,961,513 A | 10/1999 | Swanson et al. |
| 5,964,757 A | 10/1999 | Ponzi et al. |
| 5,967,976 A | 10/1999 | Larsen et al. |
| 5,967,978 A | 10/1999 | Littmann et al. |
| 5,967,984 A | 10/1999 | Chu et al. |
| 5,971,975 A | 10/1999 | Mills et al. |
| 5,972,026 A | 10/1999 | Laufer et al. |
| 5,980,484 A | 11/1999 | Ressemann et al. |
| 5,980,486 A | 11/1999 | Enger |
| 5,980,563 A | 11/1999 | Tu et al. |
| 5,989,208 A | 11/1999 | Nita et al. |
| 5,989,284 A | 11/1999 | Laufer |
| 5,993,462 A | 11/1999 | Pomeranz et al. |
| 5,997,497 A | 12/1999 | Nita et al. |
| 5,999,678 A | 12/1999 | Murphy-Chutorian et al. |
| 6,004,269 A | 12/1999 | Crowley et al. |
| 6,004,291 A | 12/1999 | Ressemann et al. |
| 6,004,316 A | 12/1999 | Laufer et al. |
| 6,007,514 A | 12/1999 | Nita |
| 6,010,522 A | 1/2000 | Barbut et al. |
| 6,013,033 A | 1/2000 | Berger et al. |
| 6,013,069 A | 1/2000 | Sirhan et al. |
| 6,014,590 A | 1/2000 | Whayne et al. |
| 6,022,309 A | 2/2000 | Celliers et al. |
| 6,022,343 A | 2/2000 | Johnson et al. |
| 6,024,722 A | 2/2000 | Rau et al. |
| 6,024,740 A | 2/2000 | Lesh et al. |
| 6,027,475 A | 2/2000 | Sirhan et al. |
| 6,030,405 A | 2/2000 | Zarbatany et al. |
| 6,030,611 A | 2/2000 | Gorecki et al. |
| 6,032,675 A | 3/2000 | Rubinsky et al. |
| 6,033,397 A | 3/2000 | Laufer et al. |
| 6,033,398 A | 3/2000 | Farley et al. |
| 6,036,687 A | 3/2000 | Laufer et al. |
| 6,036,689 A | 3/2000 | Tu et al. |
| 6,036,715 A | 3/2000 | Yock |
| 6,039,699 A | 3/2000 | Viera |
| 6,041,260 A | 3/2000 | Stern et al. |
| 6,048,338 A | 4/2000 | Larson et al. |
| 6,050,994 A | 4/2000 | Sherman et al. |
| 6,056,744 A | 5/2000 | Edwards |
| 6,056,746 A | 5/2000 | Goble et al. |
| 6,059,748 A | 5/2000 | Teirstein et al. |
| 6,063,085 A | 5/2000 | Tay et al. |
| 6,066,096 A | 5/2000 | Smith et al. |
| 6,066,114 A | 5/2000 | Goodin et al. |
| 6,066,139 A | 5/2000 | Ryan et al. |
| 6,066,144 A | 5/2000 | Wolf et al. |
| 6,068,638 A | 5/2000 | Makower |
| 6,068,653 A | 5/2000 | Lafontaine |
| 6,071,277 A | 6/2000 | Farley et al. |
| 6,071,278 A | 6/2000 | Panescu et al. |
| 6,078,839 A | 6/2000 | Carson |
| 6,079,414 A | 6/2000 | Roth |
| 6,080,171 A | 6/2000 | Keith et al. |
| 6,081,749 A | 6/2000 | Ingle et al. |
| 6,086,581 A | 7/2000 | Reynolds et al. |
| 6,093,166 A | 7/2000 | Knudson et al. |
| 6,096,021 A | 8/2000 | Helm et al. |
| 6,099,526 A | 8/2000 | Whayne et al. |
| 6,102,890 A | 8/2000 | Stivland et al. |
| 6,102,908 A | 8/2000 | Tu et al. |
| 6,106,477 A | 8/2000 | Miesel et al. |
| 6,110,187 A | 8/2000 | Donlon |
| 6,114,311 A | 9/2000 | Parmacek et al. |
| 6,117,101 A | 9/2000 | Diederich et al. |
| 6,117,128 A | 9/2000 | Gregory |
| 6,120,476 A | 9/2000 | Fung et al. |
| 6,120,516 A | 9/2000 | Selmon et al. |
| 6,121,775 A | 9/2000 | Pearlman |
| 6,123,679 A | 9/2000 | Lafaut et al. |
| 6,123,682 A | 9/2000 | Knudson et al. |
| 6,123,702 A | 9/2000 | Swanson et al. |
| 6,123,703 A | 9/2000 | Tu et al. |
| 6,123,718 A | 9/2000 | Tu et al. |
| 6,129,708 A | 10/2000 | Enger |
| 6,129,725 A | 10/2000 | Tu et al. |
| 6,135,997 A | 10/2000 | Laufer et al. |

(56) References Cited

U.S. PATENT DOCUMENTS

| | | | |
|---|---|---|---|
| 6,139,510 A | 10/2000 | Palermo |
| 6,142,991 A | 11/2000 | Schatzberger et al. |
| 6,142,993 A | 11/2000 | Whayne et al. |
| 6,149,647 A | 11/2000 | Tu et al. |
| 6,152,899 A | 11/2000 | Farley et al. |
| 6,152,909 A | 11/2000 | Bagaoisan et al. |
| 6,152,912 A | 11/2000 | Jansen et al. |
| 6,156,046 A | 12/2000 | Passafaro et al. |
| 6,158,250 A | 12/2000 | Tibbals et al. |
| 6,159,187 A | 12/2000 | Park et al. |
| 6,159,225 A | 12/2000 | Makower |
| 6,161,048 A | 12/2000 | Sluijter et al. |
| 6,162,184 A | 12/2000 | Swanson et al. |
| 6,165,163 A | 12/2000 | Chien et al. |
| 6,165,172 A | 12/2000 | Farley et al. |
| 6,165,187 A | 12/2000 | Reger et al. |
| 6,168,594 B1 | 1/2001 | Lafontaine et al. |
| 6,171,279 B1 | 1/2001 | Hilaire et al. |
| 6,171,321 B1 | 1/2001 | Gifford, III et al. |
| 6,179,832 B1 | 1/2001 | Jones et al. |
| 6,179,835 B1 | 1/2001 | Panescu et al. |
| 6,179,859 B1 | 1/2001 | Bates et al. |
| 6,183,468 B1 | 2/2001 | Swanson et al. |
| 6,183,486 B1 | 2/2001 | Snow et al. |
| 6,190,358 B1 | 2/2001 | Fitzmaurice et al. |
| 6,190,379 B1 | 2/2001 | Heuser et al. |
| 6,191,862 B1 | 2/2001 | Swanson et al. |
| 6,193,686 B1 | 2/2001 | Estrada et al. |
| 6,197,021 B1 | 3/2001 | Panescu et al. |
| 6,200,266 B1 | 3/2001 | Shokrollahi et al. |
| 6,203,537 B1 | 3/2001 | Adrian |
| 6,203,561 B1 | 3/2001 | Ramee et al. |
| 6,210,406 B1 | 4/2001 | Webster |
| 6,211,247 B1 | 4/2001 | Goodman |
| 6,217,576 B1 | 4/2001 | Tu et al. |
| 6,219,577 B1 | 4/2001 | Brown, III et al. |
| 6,228,076 B1 | 5/2001 | Winston et al. |
| 6,228,109 B1 | 5/2001 | Tu et al. |
| 6,231,516 B1 | 5/2001 | Keilman et al. |
| 6,231,587 B1 | 5/2001 | Makower |
| 6,235,044 B1 | 5/2001 | Root et al. |
| 6,236,883 B1 | 5/2001 | Ciaccio et al. |
| 6,237,605 B1 | 5/2001 | Vaska et al. |
| 6,238,389 B1 | 5/2001 | Paddock et al. |
| 6,238,392 B1 | 5/2001 | Long |
| 6,241,666 B1 | 6/2001 | Pomeranz et al. |
| 6,241,753 B1 | 6/2001 | Knowlton |
| 6,245,020 B1 | 6/2001 | Moore et al. |
| 6,245,045 B1 | 6/2001 | Stratienko |
| 6,246,914 B1 | 6/2001 | de la Rama et al. |
| 6,248,126 B1 | 6/2001 | Lesser et al. |
| 6,251,128 B1 | 6/2001 | Knopp et al. |
| 6,258,087 B1 | 7/2001 | Edwards et al. |
| 6,273,879 B1 | 8/2001 | Keith et al. |
| 6,273,886 B1 | 8/2001 | Edwards et al. |
| 6,280,466 B1 | 8/2001 | Kugler et al. |
| 6,283,935 B1 | 9/2001 | Laufer et al. |
| 6,283,959 B1 | 9/2001 | Lalonde et al. |
| 6,284,743 B1 | 9/2001 | Parmacek et al. |
| 6,287,323 B1 | 9/2001 | Hammerslag |
| 6,290,696 B1 | 9/2001 | Lafontaine |
| 6,292,695 B1 | 9/2001 | Webster, Jr. et al. |
| 6,293,942 B1 | 9/2001 | Goble et al. |
| 6,293,943 B1 | 9/2001 | Panescu et al. |
| 6,296,619 B1 | 10/2001 | Brisken et al. |
| 6,298,256 B1 | 10/2001 | Meyer |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,317,615 B1 | 11/2001 | KenKnight et al. |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,797 B1 | 12/2001 | Stewart et al. |
| 6,325,799 B1 | 12/2001 | Goble |
| 6,328,699 B1 | 12/2001 | Eigler et al. |
| 6,344,029 B1 | 2/2002 | Estrada et al. |
| 6,344,045 B1 * | 2/2002 | Lim et al. ................... 606/108 |
| 6,346,074 B1 | 2/2002 | Roth |
| 6,346,104 B2 | 2/2002 | Daly et al. |
| 6,350,248 B1 | 2/2002 | Knudson et al. |
| 6,350,276 B1 | 2/2002 | Knowlton |
| 6,353,751 B1 | 3/2002 | Swanson et al. |
| 6,355,029 B1 | 3/2002 | Joye et al. |
| 6,357,447 B1 | 3/2002 | Swanson et al. |
| 6,361,519 B1 | 3/2002 | Knudson et al. |
| 6,361,529 B1 | 3/2002 | Goodin et al. |
| 6,364,840 B1 | 4/2002 | Crowley |
| 6,371,965 B2 | 4/2002 | Gifford, III et al. |
| 6,375,668 B1 | 4/2002 | Gifford et al. |
| 6,377,854 B1 | 4/2002 | Knowlton |
| 6,377,855 B1 | 4/2002 | Knowlton |
| 6,379,352 B1 | 4/2002 | Reynolds et al. |
| 6,379,373 B1 | 4/2002 | Sawhney et al. |
| 6,381,497 B1 | 4/2002 | Knowlton |
| 6,381,498 B1 | 4/2002 | Knowlton |
| 6,383,151 B1 | 5/2002 | Diederich et al. |
| 6,387,105 B1 | 5/2002 | Gifford, III et al. |
| 6,387,380 B1 | 5/2002 | Knowlton |
| 6,389,311 B1 | 5/2002 | Whayne et al. |
| 6,389,314 B2 | 5/2002 | Feiring |
| 6,391,024 B1 | 5/2002 | Sun et al. |
| 6,394,096 B1 | 5/2002 | Constantz |
| 6,394,956 B1 | 5/2002 | Chandrasekaran et al. |
| 6,398,780 B1 | 6/2002 | Farley et al. |
| 6,398,782 B1 | 6/2002 | Pecor et al. |
| 6,398,792 B1 | 6/2002 | O'Connor |
| 6,401,720 B1 | 6/2002 | Stevens et al. |
| 6,402,719 B1 | 6/2002 | Ponzi et al. |
| 6,405,090 B1 | 6/2002 | Knowlton |
| 6,409,723 B1 | 6/2002 | Edwards |
| 6,409,863 B1 | 6/2002 | Williams et al. |
| 6,413,255 B1 | 7/2002 | Stern |
| 6,421,559 B1 | 7/2002 | Pearlman |
| 6,423,057 B1 | 7/2002 | He et al. |
| 6,425,867 B1 | 7/2002 | Vaezy et al. |
| 6,425,912 B1 | 7/2002 | Knowlton |
| 6,427,118 B1 | 7/2002 | Suzuki |
| 6,428,534 B1 | 8/2002 | Joye et al. |
| 6,428,536 B2 | 8/2002 | Panescu et al. |
| 6,430,446 B1 | 8/2002 | Knowlton |
| 6,432,102 B2 | 8/2002 | Joye et al. |
| 6,436,056 B1 | 8/2002 | Wang et al. |
| 6,438,424 B1 | 8/2002 | Knowlton |
| 6,440,125 B1 | 8/2002 | Rentrop |
| 6,442,413 B1 | 8/2002 | Silver |
| 6,443,965 B1 | 9/2002 | Gifford, III et al. |
| 6,445,939 B1 | 9/2002 | Swanson et al. |
| 6,447,479 B1 | 9/2002 | Nobuyoshi et al. |
| 6,447,505 B2 | 9/2002 | McGovern et al. |
| 6,447,509 B1 | 9/2002 | Bonnet et al. |
| 6,451,034 B1 | 9/2002 | Gifford, III et al. |
| 6,451,044 B1 | 9/2002 | Naghavi et al. |
| 6,453,202 B1 | 9/2002 | Knowlton |
| 6,454,737 B1 | 9/2002 | Nita et al. |
| 6,454,757 B1 | 9/2002 | Nita et al. |
| 6,454,775 B1 | 9/2002 | Demarais et al. |
| 6,458,098 B1 | 10/2002 | Kanesaka |
| 6,461,378 B1 | 10/2002 | Knowlton |
| 6,468,276 B1 | 10/2002 | McKay |
| 6,468,297 B1 | 10/2002 | Williams et al. |
| 6,470,216 B1 | 10/2002 | Knowlton |
| 6,470,219 B1 | 10/2002 | Edwards et al. |
| 6,471,696 B1 | 10/2002 | Berube et al. |
| 6,475,187 B1 | 11/2002 | Gerberding |
| 6,475,213 B1 | 11/2002 | Whayne et al. |
| 6,475,215 B1 | 11/2002 | Tanrisever |
| 6,475,238 B1 | 11/2002 | Fedida et al. |
| 6,477,426 B1 | 11/2002 | Fenn et al. |
| 6,480,745 B2 | 11/2002 | Nelson et al. |
| 6,481,704 B1 | 11/2002 | Koster et al. |
| 6,482,202 B1 | 11/2002 | Goble et al. |

(56) References Cited

U.S. PATENT DOCUMENTS

| | | | |
|---|---|---|---|
| 6,484,052 B1 | 11/2002 | Visuri et al. |
| 6,485,489 B2 | 11/2002 | Teirstein et al. |
| 6,488,655 B1 | 12/2002 | Wantink et al. |
| 6,488,679 B1 | 12/2002 | Swanson et al. |
| 6,489,307 B1 | 12/2002 | Phillips et al. |
| 6,491,705 B2 | 12/2002 | Gifford, III et al. |
| 6,494,891 B1 | 12/2002 | Cornish et al. |
| 6,497,711 B1 | 12/2002 | Plaia et al. |
| 6,500,172 B1 | 12/2002 | Panescu et al. |
| 6,500,174 B1 | 12/2002 | Maguire et al. |
| 6,508,765 B2 | 1/2003 | Suorsa et al. |
| 6,508,803 B1 | 1/2003 | Horikawa et al. |
| 6,508,804 B2 | 1/2003 | Sarge et al. |
| 6,508,815 B1 | 1/2003 | Strul et al. |
| 6,511,478 B1 | 1/2003 | Burnside et al. |
| 6,511,496 B1 | 1/2003 | Huter et al. |
| 6,511,500 B1 | 1/2003 | Rahme |
| 6,514,236 B1 | 2/2003 | Stratienko |
| 6,514,245 B1 | 2/2003 | Williams et al. |
| 6,514,248 B1 | 2/2003 | Eggers et al. |
| 6,517,534 B1 | 2/2003 | McGovern et al. |
| 6,517,572 B2 | 2/2003 | Kugler et al. |
| 6,522,913 B2 | 2/2003 | Swanson et al. |
| 6,522,926 B1 | 2/2003 | Kieval et al. |
| 6,524,299 B1 | 2/2003 | Tran et al. |
| 6,524,300 B2 | 2/2003 | Meglin |
| 6,527,765 B2 | 3/2003 | Kelman et al. |
| 6,527,769 B2 | 3/2003 | Langberg et al. |
| 6,533,754 B1 | 3/2003 | Hisamatsu et al. |
| 6,540,761 B2 | 4/2003 | Houser |
| 6,542,781 B1 | 4/2003 | Koblish et al. |
| 6,544,780 B1 | 4/2003 | Wang |
| 6,546,272 B1 | 4/2003 | MacKinnon et al. |
| 6,547,788 B1 | 4/2003 | Maguire et al. |
| 6,548,010 B1 | 4/2003 | Stivland et al. |
| 6,549,800 B1 | 4/2003 | Atalar et al. |
| 6,552,796 B2 | 4/2003 | Magnin et al. |
| 6,554,780 B1 | 4/2003 | Sampson et al. |
| 6,558,381 B2 | 5/2003 | Ingle et al. |
| 6,558,382 B2 | 5/2003 | Jahns et al. |
| 6,564,096 B2 | 5/2003 | Mest |
| 6,565,582 B2 | 5/2003 | Gifford, III et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,572,551 B1 | 6/2003 | Smith et al. |
| 6,572,612 B2 | 6/2003 | Stewart et al. |
| 6,575,958 B1 | 6/2003 | Happ et al. |
| 6,577,902 B1 | 6/2003 | Laufer et al. |
| 6,579,246 B2 | 6/2003 | Jacobsen et al. |
| 6,579,308 B1 | 6/2003 | Jansen et al. |
| 6,579,311 B1 | 6/2003 | Makower |
| 6,582,423 B1 | 6/2003 | Thapliyal et al. |
| 6,589,207 B2 | 7/2003 | El-Nounou |
| 6,589,238 B2 | 7/2003 | Edwards et al. |
| 6,592,526 B1 | 7/2003 | Lenker |
| 6,592,567 B1 | 7/2003 | Levin et al. |
| 6,592,569 B2 | 7/2003 | Bigus et al. |
| 6,595,959 B1 | 7/2003 | Stratienko |
| 6,600,956 B2 | 7/2003 | Maschino et al. |
| 6,602,242 B1 | 8/2003 | Fung et al. |
| 6,602,246 B1 | 8/2003 | Joye et al. |
| 6,605,057 B2 | 8/2003 | Fitzmaurice et al. |
| 6,605,084 B2 | 8/2003 | Acker et al. |
| 6,623,448 B2 | 9/2003 | Slater |
| 6,623,452 B2 | 9/2003 | Chien et al. |
| 6,623,453 B1 | 9/2003 | Guibert et al. |
| 6,632,193 B1 | 10/2003 | Davison et al. |
| 6,632,196 B1 | 10/2003 | Houser |
| 6,635,029 B1 | 10/2003 | Venturelli |
| 6,645,223 B2 | 11/2003 | Boyle et al. |
| 6,648,854 B1 | 11/2003 | Patterson et al. |
| 6,648,878 B2 | 11/2003 | Lafontaine |
| 6,648,879 B2 | 11/2003 | Joye et al. |
| 6,651,672 B2 | 11/2003 | Roth |
| 6,652,513 B2 | 11/2003 | Panescu et al. |
| 6,652,515 B1 | 11/2003 | Maguire et al. |
| 6,656,136 B1 | 12/2003 | Weng et al. |
| 6,658,279 B2 | 12/2003 | Swanson et al. |
| 6,659,981 B2 | 12/2003 | Stewart et al. |
| 6,666,858 B2 | 12/2003 | Lafontaine |
| 6,666,863 B2 | 12/2003 | Wentzel et al. |
| 6,669,655 B1 | 12/2003 | Acker et al. |
| 6,669,692 B1 | 12/2003 | Nelson et al. |
| 6,673,040 B1 | 1/2004 | Samson et al. |
| 6,673,064 B1 | 1/2004 | Rentrop |
| 6,673,066 B2 | 1/2004 | Werneth |
| 6,673,090 B2 | 1/2004 | Root et al. |
| 6,673,101 B1 | 1/2004 | Fitzgerald et al. |
| 6,673,290 B1 | 1/2004 | Whayne et al. |
| 6,676,678 B2 | 1/2004 | Gifford, III et al. |
| 6,679,268 B2 | 1/2004 | Stevens et al. |
| 6,681,773 B2 | 1/2004 | Murphy et al. |
| 6,682,541 B1 | 1/2004 | Gifford, III et al. |
| 6,684,098 B2 | 1/2004 | Oshio et al. |
| 6,685,732 B2 | 2/2004 | Kramer |
| 6,685,733 B1 | 2/2004 | Dae et al. |
| 6,689,086 B1 | 2/2004 | Nita et al. |
| 6,689,148 B2 | 2/2004 | Sawhney et al. |
| 6,690,181 B1 | 2/2004 | Dowdeswell et al. |
| 6,692,490 B1 | 2/2004 | Edwards |
| 6,695,812 B2 | 2/2004 | Estrada et al. |
| 6,695,830 B2 | 2/2004 | Vigil et al. |
| 6,695,857 B2 | 2/2004 | Gifford, III et al. |
| 6,695,863 B1 * | 2/2004 | Ramzipoor et al. .......... 606/194 |
| 6,699,241 B2 | 3/2004 | Rappaport et al. |
| 6,699,257 B2 | 3/2004 | Gifford, III et al. |
| 6,702,748 B1 | 3/2004 | Nita et al. |
| 6,702,811 B2 | 3/2004 | Stewart et al. |
| 6,706,010 B1 | 3/2004 | Miki et al. |
| 6,706,011 B1 | 3/2004 | Murphy-Chutorian et al. |
| 6,706,037 B2 | 3/2004 | Zvuloni et al. |
| 6,709,431 B2 | 3/2004 | Lafontaine |
| 6,711,429 B1 | 3/2004 | Gilboa et al. |
| 6,712,815 B2 | 3/2004 | Sampson et al. |
| 6,714,822 B2 | 3/2004 | King et al. |
| 6,716,184 B2 | 4/2004 | Vaezy et al. |
| 6,720,350 B2 | 4/2004 | Kunz et al. |
| 6,723,043 B2 | 4/2004 | Kleeman et al. |
| 6,723,064 B2 | 4/2004 | Babaev |
| 6,733,487 B2 | 5/2004 | Keith et al. |
| 6,736,811 B2 | 5/2004 | Panescu et al. |
| 6,743,184 B2 | 6/2004 | Sampson et al. |
| 6,746,401 B2 | 6/2004 | Panescu |
| 6,746,423 B1 | 6/2004 | Wantink |
| 6,746,464 B1 | 6/2004 | Makower |
| 6,746,474 B2 | 6/2004 | Saadat |
| 6,748,953 B2 | 6/2004 | Sherry et al. |
| 6,749,607 B2 | 6/2004 | Edwards et al. |
| 6,752,805 B2 | 6/2004 | Maguire et al. |
| 6,760,616 B2 | 7/2004 | Hoey et al. |
| 6,763,261 B2 | 7/2004 | Casscells, III et al. |
| 6,764,501 B2 | 7/2004 | Ganz |
| 6,769,433 B2 | 8/2004 | Zikorus et al. |
| 6,770,070 B1 | 8/2004 | Balbierz |
| 6,771,996 B2 | 8/2004 | Bowe et al. |
| 6,773,433 B2 | 8/2004 | Stewart et al. |
| 6,786,900 B2 | 9/2004 | Joye et al. |
| 6,786,901 B2 | 9/2004 | Joye et al. |
| 6,786,904 B2 | 9/2004 | Döscher et al. |
| 6,788,977 B2 | 9/2004 | Fenn et al. |
| 6,790,206 B2 | 9/2004 | Panescu |
| 6,790,222 B2 | 9/2004 | Kugler et al. |
| 6,796,981 B2 | 9/2004 | Wham et al. |
| 6,797,933 B1 | 9/2004 | Mendis et al. |
| 6,797,960 B1 | 9/2004 | Spartiotis et al. |
| 6,800,075 B2 | 10/2004 | Mische et al. |
| 6,802,857 B1 | 10/2004 | Walsh et al. |
| 6,807,444 B2 | 10/2004 | Tu et al. |
| 6,811,550 B2 | 11/2004 | Holland et al. |
| 6,813,520 B2 | 11/2004 | Truckai et al. |
| 6,814,730 B2 | 11/2004 | Li |
| 6,814,733 B2 | 11/2004 | Schwartz et al. |
| 6,823,205 B1 | 11/2004 | Jara |

(56) References Cited

U.S. PATENT DOCUMENTS

| | | |
|---|---|---|
| 6,824,516 B2 | 11/2004 | Batten et al. |
| 6,827,726 B2 | 12/2004 | Parodi |
| 6,827,926 B2 | 12/2004 | Robinson et al. |
| 6,829,497 B2 | 12/2004 | Mogul |
| 6,830,568 B1 | 12/2004 | Kesten et al. |
| 6,837,886 B2 | 1/2005 | Collins et al. |
| 6,837,888 B2 | 1/2005 | Ciarrocca et al. |
| 6,845,267 B2 | 1/2005 | Harrison et al. |
| 6,847,848 B2 | 1/2005 | Sterzer |
| 6,849,073 B2 | 2/2005 | Hoey et al. |
| 6,849,075 B2 | 2/2005 | Bertolero et al. |
| 6,853,425 B2 | 2/2005 | Kim et al. |
| 6,855,123 B2 | 2/2005 | Nita |
| 6,855,143 B2 | 2/2005 | Davison |
| 6,869,431 B2 | 3/2005 | Maguire et al. |
| 6,872,183 B2 | 3/2005 | Sampson et al. |
| 6,884,260 B2 | 4/2005 | Kugler et al. |
| 6,887,219 B2 | 5/2005 | Wantink |
| 6,889,694 B2 | 5/2005 | Hooven |
| 6,890,318 B2 | 5/2005 | Wantink |
| 6,893,436 B2 | 5/2005 | Woodard et al. |
| 6,895,077 B2 | 5/2005 | Karellas et al. |
| 6,895,265 B2 | 5/2005 | Silver |
| 6,898,454 B2 | 5/2005 | Atalar et al. |
| 6,899,711 B2 | 5/2005 | Stewart et al. |
| 6,899,718 B2 | 5/2005 | Gifford, III et al. |
| 6,905,494 B2 | 6/2005 | Yon et al. |
| 6,908,462 B2 | 6/2005 | Joye et al. |
| 6,909,009 B2 | 6/2005 | Koridze |
| 6,911,026 B1 | 6/2005 | Hall et al. |
| 6,915,806 B2 | 7/2005 | Pacek et al. |
| 6,923,805 B1 | 8/2005 | LaFontaine et al. |
| 6,926,246 B2 | 8/2005 | Ginggen |
| 6,926,713 B2 | 8/2005 | Rioux et al. |
| 6,926,716 B2 | 8/2005 | Baker et al. |
| 6,929,009 B2 | 8/2005 | Makower et al. |
| 6,929,632 B2 | 8/2005 | Nita et al. |
| 6,929,639 B2 | 8/2005 | Lafontaine |
| 6,932,776 B2 | 8/2005 | Carr |
| 6,936,047 B2 | 8/2005 | Nasab et al. |
| 6,942,620 B2 | 9/2005 | Nita et al. |
| 6,942,657 B2 | 9/2005 | Sinofsky et al. |
| 6,942,677 B2 | 9/2005 | Nita et al. |
| 6,942,692 B2 | 9/2005 | Landau et al. |
| 6,942,097 B2 | 9/2005 | Stewart et al. |
| 6,949,121 B1 | 9/2005 | Laguna |
| 6,952,615 B2 | 10/2005 | Satake |
| 6,953,425 B2 | 10/2005 | Brister |
| 6,955,174 B2 | 10/2005 | Joye et al. |
| 6,955,175 B2 | 10/2005 | Stevens et al. |
| 6,959,711 B2 | 11/2005 | Murphy et al. |
| 6,960,207 B2 | 11/2005 | Vanney et al. |
| 6,962,584 B1 | 11/2005 | Stone et al. |
| 6,964,660 B2 | 11/2005 | Maguire et al. |
| 6,966,908 B2 | 11/2005 | Maguire et al. |
| 6,972,015 B2 | 12/2005 | Joye et al. |
| 6,972,024 B1 | 12/2005 | Kilpatrick et al. |
| 6,974,456 B2 | 12/2005 | Edwards et al. |
| 6,978,174 B2 | 12/2005 | Gelfand et al. |
| 6,979,329 B2 | 12/2005 | Burnside et al. |
| 6,979,420 B2 | 12/2005 | Weber |
| 6,984,238 B2 | 1/2006 | Gifford, III et al. |
| 6,985,774 B2 | 1/2006 | Kieval et al. |
| 6,986,739 B2 | 1/2006 | Warren et al. |
| 6,989,009 B2 | 1/2006 | Lafontaine |
| 6,989,010 B2 | 1/2006 | Francischelli et al. |
| 6,991,617 B2 | 1/2006 | Hektner et al. |
| 7,001,358 B2 | 2/2006 | Fitzmaurice et al. |
| 7,001,378 B2 | 2/2006 | Yon et al. |
| 7,006,858 B2 | 2/2006 | Silver et al. |
| 7,018,372 B2 | 3/2006 | Casey et al. |
| 7,022,105 B1 | 4/2006 | Edwards |
| 7,022,120 B2 | 4/2006 | Lafontaine |
| 7,025,767 B2 | 4/2006 | Schaefer et al. |
| 7,033,322 B2 | 4/2006 | Silver |
| 7,033,372 B1 | 4/2006 | Cahalan |
| 7,037,291 B2 | 5/2006 | Lee et al. |
| 7,041,098 B2 | 5/2006 | Farley et al. |
| 7,050,848 B2 | 5/2006 | Hoey et al. |
| 7,063,670 B2 | 6/2006 | Sampson et al. |
| 7,063,679 B2 | 6/2006 | Maguire et al. |
| 7,063,719 B2 | 6/2006 | Jansen et al. |
| 7,066,895 B2 | 6/2006 | Podany |
| 7,066,900 B2 | 6/2006 | Botto et al. |
| 7,066,904 B2 | 6/2006 | Rosenthal et al. |
| 7,072,720 B2 | 7/2006 | Puskas |
| 7,074,217 B2 | 7/2006 | Strul et al. |
| 7,081,112 B2 | 7/2006 | Joye et al. |
| 7,081,114 B2 | 7/2006 | Rashidi |
| 7,083,614 B2 | 8/2006 | Fjield et al. |
| 7,084,276 B2 | 8/2006 | Vu et al. |
| 7,087,026 B2 | 8/2006 | Callister et al. |
| 7,087,051 B2 | 8/2006 | Bourne et al. |
| 7,087,052 B2 | 8/2006 | Sampson et al. |
| 7,087,053 B2 | 8/2006 | Vanney |
| 7,089,065 B2 | 8/2006 | Westlund et al. |
| 7,097,641 B1 | 8/2006 | Arless et al. |
| 7,100,614 B2 | 9/2006 | Stevens et al. |
| 7,101,368 B2 | 9/2006 | Lafontaine |
| 7,104,983 B2 | 9/2006 | Grasso, III et al. |
| 7,104,987 B2 | 9/2006 | Biggs et al. |
| 7,108,715 B2 | 9/2006 | Lawrence-Brown et al. |
| 7,112,196 B2 | 9/2006 | Brosch et al. |
| 7,112,198 B2 | 9/2006 | Satake |
| 7,112,211 B2 | 9/2006 | Gifford, III et al. |
| 7,122,019 B1 | 10/2006 | Kesten et al. |
| 7,122,033 B2 | 10/2006 | Wood |
| 7,134,438 B2 | 11/2006 | Makower et al. |
| 7,137,963 B2 | 11/2006 | Nita et al. |
| 7,137,980 B2 | 11/2006 | Buysse et al. |
| 7,153,315 B2 | 12/2006 | Miller |
| 7,155,271 B2 | 12/2006 | Halperin et al. |
| 7,157,491 B2 | 1/2007 | Mewshaw et al. |
| 7,157,492 B2 | 1/2007 | Mewshaw et al. |
| 7,158,832 B2 | 1/2007 | Kieval et al. |
| 7,160,296 B2 | 1/2007 | Pearson et al. |
| 7,162,303 B2 | 1/2007 | Levin et al. |
| 7,165,551 B2 | 1/2007 | Edwards et al. |
| 7,169,144 B2 | 1/2007 | Hoey et al. |
| 7,169,162 B2 | 1/2007 | Garakani |
| 7,172,589 B2 | 2/2007 | Lafontaine |
| 7,172,610 B2 | 2/2007 | Heitzmann et al. |
| 7,181,261 B2 | 2/2007 | Silver et al. |
| 7,184,811 B2 | 2/2007 | Phan et al. |
| 7,184,827 B1 | 2/2007 | Edwards |
| 7,189,227 B2 | 3/2007 | Lafontaine |
| 7,192,427 B2 | 3/2007 | Chapelon et al. |
| 7,192,586 B2 | 3/2007 | Bander |
| 7,195,611 B1 | 3/2007 | Simpson et al. |
| 7,197,354 B2 | 3/2007 | Sobe |
| 7,198,632 B2 | 4/2007 | Lim et al. |
| 7,200,445 B1 | 4/2007 | Dalbec et al. |
| 7,201,749 B2 | 4/2007 | Govari et al. |
| 7,203,537 B2 | 4/2007 | Mower |
| 7,214,234 B2 | 5/2007 | Rapacki et al. |
| 7,220,233 B2 | 5/2007 | Nita et al. |
| 7,220,239 B2 | 5/2007 | Wilson et al. |
| 7,220,257 B1 | 5/2007 | Lafontaine |
| 7,220,270 B2 | 5/2007 | Sawhney et al. |
| 7,232,458 B2 | 6/2007 | Saadat |
| 7,232,459 B2 | 6/2007 | Greenberg et al. |
| 7,238,184 B2 | 7/2007 | Megerman et al. |
| 7,241,273 B2 | 7/2007 | Maguire et al. |
| 7,241,736 B2 | 7/2007 | Hunter et al. |
| 7,247,141 B2 | 7/2007 | Makin et al. |
| 7,250,041 B2 | 7/2007 | Chiu et al. |
| 7,250,440 B2 | 7/2007 | Mewshaw et al. |
| 7,252,664 B2 | 8/2007 | Nasab et al. |
| 7,252,679 B2 | 8/2007 | Fischell et al. |
| 7,264,619 B2 | 9/2007 | Venturelli |
| 7,279,600 B2 | 10/2007 | Mewshaw et al. |
| 7,280,863 B2 | 10/2007 | Shachar |
| 7,282,213 B2 | 10/2007 | Schroeder et al. |
| 7,285,119 B2 | 10/2007 | Stewart et al. |

(56) References Cited

U.S. PATENT DOCUMENTS

| | | |
|---|---|---|
| 7,285,120 B2 | 10/2007 | Im et al. |
| 7,288,089 B2 | 10/2007 | Yon et al. |
| 7,288,096 B2 | 10/2007 | Chin |
| 7,291,146 B2 | 11/2007 | Steinke et al. |
| 7,293,562 B2 | 11/2007 | Malecki et al. |
| 7,294,124 B2 | 11/2007 | Eidenschink |
| 7,294,125 B2 | 11/2007 | Phalen et al. |
| 7,294,126 B2 | 11/2007 | Sampson et al. |
| 7,294,127 B2 | 11/2007 | Leung et al. |
| 7,297,131 B2 | 11/2007 | Nita |
| 7,297,475 B2 | 11/2007 | Koiwai et al. |
| 7,300,433 B2 | 11/2007 | Lane et al. |
| 7,301,108 B2 | 11/2007 | Egitto et al. |
| 7,310,150 B2 | 12/2007 | Guillermo et al. |
| 7,313,430 B2 | 12/2007 | Urquhart et al. |
| 7,314,483 B2 | 1/2008 | Landau et al. |
| 7,317,077 B2 | 1/2008 | Averback et al. |
| 7,323,006 B2 | 1/2008 | Andreas et al. |
| 7,326,206 B2 | 2/2008 | Paul et al. |
| 7,326,226 B2 | 2/2008 | Root et al. |
| 7,326,235 B2 | 2/2008 | Edwards |
| 7,326,237 B2 | 2/2008 | DePalma et al. |
| 7,329,236 B2 | 2/2008 | Kesten et al. |
| 7,335,180 B2 | 2/2008 | Nita et al. |
| 7,335,192 B2 | 2/2008 | Keren et al. |
| 7,338,467 B2 | 3/2008 | Lutter |
| 7,341,570 B2 | 3/2008 | Keren et al. |
| 7,343,195 B2 | 3/2008 | Strommer et al. |
| 7,347,857 B2 | 3/2008 | Anderson et al. |
| 7,348,003 B2 | 3/2008 | Salcedo et al. |
| 7,352,593 B2 | 4/2008 | Zeng et al. |
| 7,354,927 B2 | 4/2008 | Vu |
| 7,359,732 B2 | 4/2008 | Kim et al. |
| 7,361,341 B2 | 4/2008 | Salcedo et al. |
| 7,364,566 B2 | 4/2008 | Elkins et al. |
| 7,367,967 B2 | 5/2008 | Eidenschink |
| 7,367,970 B2 | 5/2008 | Govari et al. |
| 7,367,975 B2 | 5/2008 | Malecki et al. |
| 7,371,231 B2 | 5/2008 | Rioux et al. |
| 7,387,126 B2 | 6/2008 | Cox et al. |
| 7,393,338 B2 | 7/2008 | Nita |
| 7,396,355 B2 | 7/2008 | Goldman et al. |
| 7,402,151 B2 | 7/2008 | Rosenman et al. |
| 7,402,312 B2 | 7/2008 | Rosen et al. |
| 7,404,824 B1 | 7/2008 | Webler et al. |
| 7,406,970 B2 | 8/2008 | Zikorus et al. |
| 7,407,502 B2 | 8/2008 | Strul et al. |
| 7,407,506 B2 | 8/2008 | Makower |
| 7,407,671 B2 | 8/2008 | McBride et al. |
| 7,408,021 B2 | 8/2008 | Averback et al. |
| 7,410,486 B2 | 8/2008 | Fuimaono et al. |
| 7,413,556 B2 | 8/2008 | Zhang et al. |
| 7,425,212 B1 | 9/2008 | Danek et al. |
| 7,426,409 B2 | 9/2008 | Casscells, III et al. |
| 7,435,248 B2 | 10/2008 | Taimisto et al. |
| 7,447,453 B2 | 11/2008 | Kim et al. |
| 7,449,018 B2 | 11/2008 | Kramer |
| 7,452,538 B2 | 11/2008 | Ni et al. |
| 7,473,890 B2 | 1/2009 | Grier et al. |
| 7,476,384 B2 | 1/2009 | Ni et al. |
| 7,479,157 B2 | 1/2009 | Weber et al. |
| 7,481,803 B2 | 1/2009 | Kesten et al. |
| 7,485,104 B2 | 2/2009 | Kieval |
| 7,486,805 B2 | 2/2009 | Krattiger |
| 7,487,780 B2 | 2/2009 | Hooven |
| 7,493,154 B2 | 2/2009 | Bonner et al. |
| 7,494,485 B2 | 2/2009 | Beck et al. |
| 7,494,486 B2 | 2/2009 | Mische et al. |
| 7,494,488 B2 | 2/2009 | Weber |
| 7,494,661 B2 | 2/2009 | Sanders |
| 7,495,439 B2 | 2/2009 | Wiggins |
| 7,497,858 B2 | 3/2009 | Chapelon et al. |
| 7,499,745 B2 | 3/2009 | Littrup et al. |
| 7,500,985 B2 | 3/2009 | Saadat |
| 7,505,812 B1 | 3/2009 | Eggers et al. |
| 7,505,816 B2 | 3/2009 | Schmeling et al. |
| 7,507,233 B2 | 3/2009 | Littrup et al. |
| 7,507,235 B2 | 3/2009 | Keogh et al. |
| 7,511,494 B2 | 3/2009 | Wedeen |
| 7,512,445 B2 | 3/2009 | Truckai et al. |
| 7,527,643 B2 | 5/2009 | Case et al. |
| 7,529,589 B2 | 5/2009 | Williams et al. |
| 7,540,852 B2 | 6/2009 | Nita et al. |
| 7,540,870 B2 | 6/2009 | Babaev |
| 7,544,201 B2 | 6/2009 | Pepper |
| RE40,863 E | 7/2009 | Tay et al. |
| 7,556,624 B2 | 7/2009 | Laufer et al. |
| 7,556,642 B2 | 7/2009 | Trotta |
| 7,558,625 B2 | 7/2009 | Levin et al. |
| 7,563,247 B2 | 7/2009 | Maguire et al. |
| 7,566,319 B2 | 7/2009 | McAuley et al. |
| 7,569,052 B2 | 8/2009 | Phan et al. |
| 7,582,111 B2 | 9/2009 | Krolik et al. |
| 7,584,004 B2 | 9/2009 | Caparso et al. |
| 7,585,835 B2 | 9/2009 | Hill et al. |
| 7,591,996 B2 | 9/2009 | Hwang et al. |
| 7,597,704 B2 | 10/2009 | Frazier et al. |
| 7,598,228 B2 | 10/2009 | Hattori et al. |
| 7,599,730 B2 | 10/2009 | Hunter et al. |
| 7,603,166 B2 | 10/2009 | Casscells, III et al. |
| 7,604,608 B2 | 10/2009 | Nita et al. |
| 7,604,633 B2 | 10/2009 | Truckai et al. |
| 7,615,015 B2 | 11/2009 | Coleman |
| 7,615,072 B2 | 11/2009 | Rust et al. |
| 7,617,005 B2 | 11/2009 | Demarais et al. |
| 7,620,451 B2 | 11/2009 | Demarais et al. |
| 7,621,902 B2 | 11/2009 | Nita et al. |
| 7,621,929 B2 | 11/2009 | Nita et al. |
| 7,626,015 B2 | 12/2009 | Feinstein et al. |
| 7,626,235 B2 | 12/2009 | Kinoshita |
| 7,632,268 B2 | 12/2009 | Edwards et al. |
| 7,632,845 B2 | 12/2009 | Vu et al. |
| 7,635,383 B2 | 12/2009 | Gumm |
| 7,640,046 B2 | 12/2009 | Pastore et al. |
| 7,641,633 B2 | 1/2010 | Laufer et al. |
| 7,641,679 B2 | 1/2010 | Joye et al. |
| 7,646,544 B2 | 1/2010 | Batchko et al. |
| 7,647,115 B2 | 1/2010 | Levin et al. |
| 7,653,438 B2 | 1/2010 | Deem et al. |
| 7,655,006 B2 | 2/2010 | Sauvageau et al. |
| 7,662,114 B2 | 2/2010 | Seip et al. |
| 7,664,548 B2 | 2/2010 | Amurthur et al. |
| 7,670,279 B2 | 3/2010 | Gertner |
| 7,670,335 B2 | 3/2010 | Keidar |
| 7,671,084 B2 | 3/2010 | Mewshaw et al. |
| 7,678,104 B2 | 3/2010 | Keidar |
| 7,678,106 B2 | 3/2010 | Lee |
| 7,678,108 B2 | 3/2010 | Chrisitian et al. |
| 7,691,080 B2 | 4/2010 | Seward et al. |
| 7,699,809 B2 | 4/2010 | Urmey |
| 7,706,882 B2 | 4/2010 | Francischelli et al. |
| 7,715,912 B2 | 5/2010 | Rezai et al. |
| 7,717,853 B2 | 5/2010 | Nita |
| 7,717,909 B2 | 5/2010 | Strul et al. |
| 7,717,948 B2 | 5/2010 | Demarais et al. |
| 7,722,539 B2 | 5/2010 | Carter et al. |
| 7,725,157 B2 | 5/2010 | Dumoulin et al. |
| 7,727,178 B2 | 6/2010 | Wilson et al. |
| 7,736,317 B2 | 6/2010 | Stephens et al. |
| 7,736,360 B2 | 6/2010 | Mody et al. |
| 7,736,362 B2 | 6/2010 | Eberl et al. |
| 7,738,952 B2 | 6/2010 | Yun et al. |
| 7,740,629 B2 | 6/2010 | Anderson et al. |
| 7,741,299 B2 | 6/2010 | Feinstein et al. |
| 7,742,795 B2 | 6/2010 | Stone et al. |
| 7,744,594 B2 | 6/2010 | Yamazaki et al. |
| 7,753,907 B2 | 7/2010 | DiMatteo et al. |
| 7,756,583 B2 | 7/2010 | Demarais et al. |
| 7,758,510 B2 | 7/2010 | Nita et al. |
| 7,758,520 B2 | 7/2010 | Griffin et al. |
| 7,759,315 B2 | 7/2010 | Cuzzocrea et al. |
| 7,766,833 B2 | 8/2010 | Lee et al. |
| 7,766,878 B2 | 8/2010 | Tremaglio, Jr. et al. |
| 7,766,892 B2 | 8/2010 | Keren et al. |

(56) References Cited

U.S. PATENT DOCUMENTS

| | | |
|---|---|---|
| 7,767,844 B2 | 8/2010 | Lee et al. |
| 7,769,427 B2 | 8/2010 | Shachar |
| 7,771,372 B2 | 8/2010 | Wilson |
| 7,771,421 B2 | 8/2010 | Stewart et al. |
| 7,776,967 B2 | 8/2010 | Perry et al. |
| 7,777,486 B2 | 8/2010 | Hargreaves et al. |
| 7,780,660 B2 | 8/2010 | Bourne et al. |
| 7,789,876 B2 | 9/2010 | Zikorus et al. |
| 7,792,568 B2 | 9/2010 | Zhong et al. |
| 7,799,021 B2 | 9/2010 | Leung et al. |
| 7,803,168 B2 | 9/2010 | Gifford et al. |
| 7,806,871 B2 | 10/2010 | Li et al. |
| 7,811,265 B2 | 10/2010 | Hering et al. |
| 7,811,281 B1 | 10/2010 | Rentrop |
| 7,811,313 B2 | 10/2010 | Mon et al. |
| 7,816,511 B2 | 10/2010 | Kawashima et al. |
| 7,818,053 B2 | 10/2010 | Kassab |
| 7,819,866 B2 | 10/2010 | Bednarek |
| 7,822,460 B2 | 10/2010 | Halperin et al. |
| 7,828,837 B2 | 11/2010 | Khoury |
| 7,832,407 B2 | 11/2010 | Gertner |
| 7,833,220 B2 | 11/2010 | Mon et al. |
| 7,837,676 B2 | 11/2010 | Sinelnikov et al. |
| 7,837,720 B2 | 11/2010 | Mon |
| 7,841,978 B2 | 11/2010 | Gertner |
| 7,846,157 B2 | 12/2010 | Kozel |
| 7,846,160 B2 | 12/2010 | Payne et al. |
| 7,846,172 B2 | 12/2010 | Makower |
| 7,849,860 B2 | 12/2010 | Makower et al. |
| 7,850,685 B2 | 12/2010 | Kunis et al. |
| 7,853,333 B2 | 12/2010 | Demarais |
| 7,854,734 B2 | 12/2010 | Biggs et al. |
| 7,857,756 B2 | 12/2010 | Warren et al. |
| 7,862,565 B2 | 1/2011 | Eder et al. |
| 7,863,897 B2 | 1/2011 | Slocum, Jr. et al. |
| 7,869,854 B2 | 1/2011 | Shachar et al. |
| 7,873,417 B2 | 1/2011 | Demarais et al. |
| 7,887,538 B2 | 2/2011 | Bleich et al. |
| 7,894,905 B2 | 2/2011 | Pless et al. |
| 7,896,873 B2 | 3/2011 | Hiller et al. |
| 7,901,378 B2 | 3/2011 | Solar et al. |
| 7,901,400 B2 | 3/2011 | Wham et al. |
| 7,901,402 B2 | 3/2011 | Jones et al. |
| 7,901,420 B2 | 3/2011 | Dunn |
| 7,905,862 B2 | 3/2011 | Sampson |
| 7,918,850 B2 | 4/2011 | Govari et al. |
| 7,927,370 B2 | 4/2011 | Webler et al. |
| 7,937,143 B2 | 5/2011 | Demarais et al. |
| 7,938,830 B2 | 5/2011 | Saadat et al. |
| 7,942,874 B2 | 5/2011 | Eder et al. |
| 7,942,928 B2 | 5/2011 | Webler et al. |
| 7,946,976 B2 | 5/2011 | Gertner |
| 7,950,397 B2 | 5/2011 | Thapliyal et al. |
| 7,955,293 B2 | 6/2011 | Nita et al. |
| 7,956,613 B2 | 6/2011 | Wald |
| 7,959,627 B2 | 6/2011 | Utley et al. |
| 7,962,854 B2 | 6/2011 | Vance et al. |
| 7,967,782 B2 | 6/2011 | Laufer et al. |
| 7,967,808 B2 | 6/2011 | Fitzgerald et al. |
| 7,972,327 B2 | 7/2011 | Eberl et al. |
| 7,972,330 B2 | 7/2011 | Alejandro et al. |
| 7,983,751 B2 | 7/2011 | Zdeblick et al. |
| 8,001,976 B2 | 8/2011 | Gertner |
| 8,007,440 B2 | 8/2011 | Magnin et al. |
| 8,012,147 B2 | 9/2011 | Lafontaine |
| 8,019,435 B2 | 9/2011 | Hastings et al. |
| 8,021,362 B2 | 9/2011 | Deem et al. |
| 8,021,413 B2 | 9/2011 | Dierking et al. |
| 8,025,661 B2 | 9/2011 | Arnold et al. |
| 8,027,718 B2 | 9/2011 | Spinner et al. |
| 8,031,927 B2 | 10/2011 | Karl et al. |
| 8,033,284 B2 | 10/2011 | Porter et al. |
| 8,048,144 B2 | 11/2011 | Thistle et al. |
| 8,052,636 B2 | 11/2011 | Moll et al. |
| 8,052,700 B2 | 11/2011 | Dunn |
| 8,057,430 B2 | 11/2011 | Grovender et al. |
| 8,062,289 B2 | 11/2011 | Babaev |
| 8,075,580 B2 | 12/2011 | Makower |
| 8,080,006 B2 | 12/2011 | Lafontaine et al. |
| 8,088,127 B2 | 1/2012 | Mayse et al. |
| 8,116,883 B2 | 2/2012 | Williams et al. |
| 8,119,183 B2 | 2/2012 | O'Donoghue et al. |
| 8,120,518 B2 | 2/2012 | Jang et al. |
| 8,123,741 B2 | 2/2012 | Marrouche et al. |
| 8,128,617 B2 | 3/2012 | Bencini et al. |
| 8,131,371 B2 | 3/2012 | Demarals et al. |
| 8,131,372 B2 | 3/2012 | Levin et al. |
| 8,131,382 B2 | 3/2012 | Asada |
| 8,137,274 B2 | 3/2012 | Weng et al. |
| 8,140,170 B2 | 3/2012 | Rezai et al. |
| 8,143,316 B2 | 3/2012 | Ueno |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,830 B2 | 4/2012 | Gumm |
| 8,162,933 B2 | 4/2012 | Francischelli et al. |
| 8,175,711 B2 | 5/2012 | Demarais et al. |
| 8,187,261 B2 | 5/2012 | Watson |
| 8,190,238 B2 | 5/2012 | Moll et al. |
| 8,192,053 B2 | 6/2012 | Owen et al. |
| 8,198,611 B2 | 6/2012 | LaFontaine et al. |
| 8,214,056 B2 | 7/2012 | Hoffer et al. |
| 8,221,407 B2 | 7/2012 | Phan et al. |
| 8,226,637 B2 | 7/2012 | Satake |
| 8,231,617 B2 | 7/2012 | Satake |
| 8,241,217 B2 | 8/2012 | Chiang et al. |
| 8,257,724 B2 | 9/2012 | Cromack et al. |
| 8,257,725 B2 | 9/2012 | Cromack et al. |
| 8,260,397 B2 | 9/2012 | Ruff et al. |
| 8,263,104 B2 | 9/2012 | Ho et al. |
| 8,273,023 B2 | 9/2012 | Razavi |
| 8,277,379 B2 | 10/2012 | Lau et al. |
| 8,287,524 B2 | 10/2012 | Siegel |
| 8,287,532 B2 | 10/2012 | Carroll et al. |
| 8,292,881 B2 | 10/2012 | Brannan et al. |
| 8,293,703 B2 | 10/2012 | Averback et al. |
| 8,295,902 B2 | 10/2012 | Salahieh et al. |
| 8,295,912 B2 | 10/2012 | Gertner |
| 8,308,722 B2 | 11/2012 | Ormsby et al. |
| 8,317,776 B2 | 11/2012 | Ferren et al. |
| 8,317,810 B2 | 11/2012 | Stangenes et al. |
| 8,329,179 B2 | 12/2012 | Ni et al. |
| 8,336,705 B2 | 12/2012 | Okahisa |
| 8,343,031 B2 | 1/2013 | Gertner |
| 8,343,145 B2 | 1/2013 | Brannan |
| 8,347,891 B2 | 1/2013 | Demarais et al. |
| 8,353,945 B2 | 1/2013 | Andreas et al. |
| 8,364,237 B2 | 1/2013 | Stone et al. |
| 8,366,615 B2 | 2/2013 | Razavi |
| 8,382,697 B2 | 2/2013 | Brenneman et al. |
| 8,388,680 B2 | 3/2013 | Starksen et al. |
| 8,396,548 B2 | 3/2013 | Perry et al. |
| 8,398,629 B2 | 3/2013 | Thistle |
| 8,401,667 B2 | 3/2013 | Gustus et al. |
| 8,403,881 B2 | 3/2013 | Ferren et al. |
| 8,406,877 B2 | 3/2013 | Smith et al. |
| 8,409,172 B2 | 4/2013 | Moll et al. |
| 8,409,193 B2 | 4/2013 | Young et al. |
| 8,409,195 B2 | 4/2013 | Young |
| 8,418,362 B2 | 4/2013 | Zerfas et al. |
| 8,452,988 B2 | 5/2013 | Wang |
| 8,454,594 B2 | 6/2013 | Demarais et al. |
| 8,460,358 B2 | 6/2013 | Andreas et al. |
| 8,465,452 B2 | 6/2013 | Kassab |
| 8,469,919 B2 | 6/2013 | Ingle et al. |
| 8,473,067 B2 | 6/2013 | Hastings et al. |
| 8,480,663 B2 | 7/2013 | Ingle et al. |
| 8,485,992 B2 | 7/2013 | Griffin et al. |
| 8,486,060 B2 | 7/2013 | Kotmel et al. |
| 8,486,063 B2 | 7/2013 | Werneth et al. |
| 8,488,591 B2 | 7/2013 | Miali et al. |
| 2001/0007070 A1 | 7/2001 | Stewart et al. |

(56) References Cited

U.S. PATENT DOCUMENTS

| | | |
|---|---|---|
| 2001/0029362 A1 | 10/2001 | Sirhan et al. |
| 2001/0037085 A1 | 11/2001 | Keith et al. |
| 2001/0039419 A1 | 11/2001 | Francischelli et al. |
| 2002/0022864 A1 | 2/2002 | Mahvi et al. |
| 2002/0042639 A1 | 4/2002 | Murphy-Chutorian et al. |
| 2002/0045811 A1 | 4/2002 | Kittrell et al. |
| 2002/0045890 A1 | 4/2002 | Celliers et al. |
| 2002/0062146 A1 | 5/2002 | Makower et al. |
| 2002/0065542 A1 | 5/2002 | Lax et al. |
| 2002/0087151 A1 | 7/2002 | Mody et al. |
| 2002/0095197 A1 | 7/2002 | Lardo et al. |
| 2002/0107536 A1 | 8/2002 | Hussein |
| 2002/0147480 A1 | 10/2002 | Mamayek |
| 2002/0169444 A1 | 11/2002 | Mest et al. |
| 2002/0198520 A1 | 12/2002 | Coen et al. |
| 2003/0065317 A1 | 4/2003 | Rudie et al. |
| 2003/0092995 A1 | 5/2003 | Thompson |
| 2003/0105427 A1 | 6/2003 | Lee et al. |
| 2003/0139689 A1 | 7/2003 | Shturman et al. |
| 2003/0176837 A1 | 9/2003 | Fitzmaurice et al. |
| 2003/0195501 A1 | 10/2003 | Sherman et al. |
| 2003/0199747 A1 | 10/2003 | Michlitsch et al. |
| 2004/0010118 A1 | 1/2004 | Zerhusen et al. |
| 2004/0019348 A1 | 1/2004 | Stevens et al. |
| 2004/0024371 A1 | 2/2004 | Plicchi et al. |
| 2004/0043030 A1 | 3/2004 | Griffiths et al. |
| 2004/0059292 A1 | 3/2004 | Hisamatsu et al. |
| 2004/0064090 A1 | 4/2004 | Keren et al. |
| 2004/0073206 A1 | 4/2004 | Foley et al. |
| 2004/0088002 A1 | 5/2004 | Boyle et al. |
| 2004/0093055 A1 | 5/2004 | Bartorelli et al. |
| 2004/0106871 A1 | 6/2004 | Hunyor et al. |
| 2004/0117032 A1 | 6/2004 | Roth |
| 2004/0147915 A1 | 7/2004 | Hasebe |
| 2004/0162555 A1 | 8/2004 | Farley et al. |
| 2004/0167506 A1 | 8/2004 | Chen |
| 2004/0186356 A1 | 9/2004 | O'Malley et al. |
| 2004/0187875 A1 | 9/2004 | He et al. |
| 2004/0193211 A1 | 9/2004 | Voegele et al. |
| 2004/0220556 A1 | 11/2004 | Cooper et al. |
| 2004/0230178 A1 | 11/2004 | Wu |
| 2004/0243022 A1 | 12/2004 | Carney et al. |
| 2004/0249436 A1 | 12/2004 | Aznoian et al. |
| 2004/0253304 A1 | 12/2004 | Gross et al. |
| 2004/0267250 A1 | 12/2004 | Yon et al. |
| 2005/0010095 A1 | 1/2005 | Stewart et al. |
| 2005/0015125 A1 | 1/2005 | Mioduski et al. |
| 2005/0049552 A1 | 3/2005 | Holzapfel et al. |
| 2005/0059959 A1 | 3/2005 | Eidenschink |
| 2005/0070880 A1 | 3/2005 | Varma et al. |
| 2005/0080374 A1 | 4/2005 | Esch et al. |
| 2005/0129616 A1 | 6/2005 | Salcedo et al. |
| 2005/0137180 A1 | 6/2005 | Robinson et al. |
| 2005/0143817 A1 | 6/2005 | Hunter et al. |
| 2005/0148842 A1 | 7/2005 | Wang et al. |
| 2005/0149069 A1 | 7/2005 | Bertolero et al. |
| 2005/0149080 A1 | 7/2005 | Hunter et al. |
| 2005/0149158 A1 | 7/2005 | Hunter et al. |
| 2005/0149173 A1 | 7/2005 | Hunter et al. |
| 2005/0149175 A1 | 7/2005 | Hunter et al. |
| 2005/0154277 A1 | 7/2005 | Tang et al. |
| 2005/0154445 A1 | 7/2005 | Hunter et al. |
| 2005/0154453 A1 | 7/2005 | Hunter et al. |
| 2005/0154454 A1 | 7/2005 | Hunter et al. |
| 2005/0165389 A1 | 7/2005 | Swain et al. |
| 2005/0165391 A1 | 7/2005 | Maguire et al. |
| 2005/0165467 A1 | 7/2005 | Hunter et al. |
| 2005/0165488 A1 | 7/2005 | Hunter et al. |
| 2005/0175661 A1 | 8/2005 | Hunter et al. |
| 2005/0175662 A1 | 8/2005 | Hunter et al. |
| 2005/0175663 A1 | 8/2005 | Hunter et al. |
| 2005/0177103 A1 | 8/2005 | Hunter et al. |
| 2005/0177225 A1 | 8/2005 | Hunter et al. |
| 2005/0181004 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0182479 A1 | 8/2005 | Bonsignore et al. |
| 2005/0183728 A1 | 8/2005 | Hunter et al. |
| 2005/0186242 A1 | 8/2005 | Hunter et al. |
| 2005/0186243 A1 | 8/2005 | Hunter et al. |
| 2005/0191331 A1 | 9/2005 | Hunter et al. |
| 2005/0203410 A1 | 9/2005 | Jenkins |
| 2005/0209587 A1 | 9/2005 | Joye et al. |
| 2005/0214205 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0214268 A1 | 9/2005 | Cavanagh et al. |
| 2005/0228286 A1 | 10/2005 | Messerly et al. |
| 2005/0228415 A1 | 10/2005 | Gertner |
| 2005/0228460 A1 | 10/2005 | Levin et al. |
| 2005/0232921 A1 | 10/2005 | Rosen et al. |
| 2005/0234312 A1 | 10/2005 | Suzuki et al. |
| 2005/0245862 A1 | 11/2005 | Seward |
| 2005/0251116 A1 | 11/2005 | Steinke et al. |
| 2005/0252553 A1 | 11/2005 | Ginggen |
| 2005/0256398 A1 | 11/2005 | Hastings et al. |
| 2005/0267556 A1 | 12/2005 | Shuros et al. |
| 2006/0004323 A1 | 1/2006 | Chang et al. |
| 2006/0018949 A1 | 1/2006 | Ammon et al. |
| 2006/0024564 A1 | 2/2006 | Manclaw |
| 2006/0025765 A1 | 2/2006 | Landman et al. |
| 2006/0062786 A1 | 3/2006 | Salcedo et al. |
| 2006/0064074 A1 | 3/2006 | Mallaby |
| 2006/0083194 A1 | 4/2006 | Dhrimaj et al. |
| 2006/0089637 A1 | 4/2006 | Werneth et al. |
| 2006/0089638 A1 | 4/2006 | Carmel et al. |
| 2006/0095096 A1 | 5/2006 | DeBenedictis et al. |
| 2006/0106375 A1 | 5/2006 | Werneth et al. |
| 2006/0142696 A1 | 6/2006 | Kumoyama et al. |
| 2006/0142790 A1 | 6/2006 | Gertner |
| 2006/0147492 A1 | 7/2006 | Hunter et al. |
| 2006/0167106 A1 | 7/2006 | Zhang et al. |
| 2006/0167498 A1 | 7/2006 | DiLorenzo |
| 2006/0171895 A1 | 8/2006 | Bucay-Couto |
| 2006/0184221 A1 | 8/2006 | Stewart et al. |
| 2006/0195139 A1 | 8/2006 | Gertner |
| 2006/0206150 A1 | 9/2006 | Demarais et al. |
| 2006/0224153 A1 | 10/2006 | Fischell et al. |
| 2006/0239921 A1 | 10/2006 | Mangat et al. |
| 2006/0240070 A1 | 10/2006 | Cromack et al. |
| 2006/0247266 A1 | 11/2006 | Yamada et al. |
| 2006/0247760 A1 | 11/2006 | Ganesan et al. |
| 2006/0263393 A1 | 11/2006 | Demopulos et al. |
| 2006/0269555 A1 | 11/2006 | Salcedo et al. |
| 2006/0271111 A1 | 11/2006 | Demarais et al. |
| 2006/0287644 A1 | 12/2006 | Inganas et al. |
| 2007/0016133 A1 | 1/2007 | Pepper |
| 2007/0016184 A1 | 1/2007 | Cropper et al. |
| 2007/0016274 A1 | 1/2007 | Boveja et al. |
| 2007/0027390 A1 | 2/2007 | Maschke et al. |
| 2007/0043077 A1 | 2/2007 | Mewshaw et al. |
| 2007/0043409 A1 | 2/2007 | Brian et al. |
| 2007/0049924 A1 | 3/2007 | Rahn |
| 2007/0066972 A1 | 3/2007 | Ormsby et al. |
| 2007/0073151 A1 | 3/2007 | Lee |
| 2007/0093710 A1 | 4/2007 | Maschke |
| 2007/0100405 A1 | 5/2007 | Thompson et al. |
| 2007/0106247 A1 | 5/2007 | Burnett et al. |
| 2007/0112327 A1 | 5/2007 | Yun et al. |
| 2007/0118107 A1 | 5/2007 | Francischelli et al. |
| 2007/0129760 A1 | 6/2007 | Demarais et al. |
| 2007/0129761 A1 | 6/2007 | Demarais et al. |
| 2007/0135763 A1 | 6/2007 | Musbach et al. |
| 2007/0135875 A1 | 6/2007 | Demarais et al. |
| 2007/0142821 A1 | 6/2007 | Hennessy et al. |
| 2007/0149963 A1 | 6/2007 | Matsukuma et al. |
| 2007/0162109 A1 | 7/2007 | Davila et al. |
| 2007/0173805 A1 | 7/2007 | Weinberg et al. |
| 2007/0179496 A1 | 8/2007 | Swoyer et al. |
| 2007/0203480 A1 | 8/2007 | Mody et al. |
| 2007/0207186 A1 | 9/2007 | Scanlon et al. |

(56) References Cited

U.S. PATENT DOCUMENTS

| | | |
|---|---|---|
| 2007/0208134 A1 | 9/2007 | Hunter et al. |
| 2007/0208210 A1 | 9/2007 | Gelfand et al. |
| 2007/0208256 A1 | 9/2007 | Marilla |
| 2007/0208301 A1 | 9/2007 | Evard et al. |
| 2007/0219576 A1 | 9/2007 | Cangialosi |
| 2007/0225659 A1 | 9/2007 | Melsheimer |
| 2007/0225781 A1 | 9/2007 | Saadat et al. |
| 2007/0233170 A1 | 10/2007 | Gertner |
| 2007/0239062 A1 | 10/2007 | Chopra et al. |
| 2007/0248639 A1 | 10/2007 | Demopulos et al. |
| 2007/0249703 A1 | 10/2007 | Mewshaw et al. |
| 2007/0254833 A1 | 11/2007 | Hunter et al. |
| 2007/0265687 A1 | 11/2007 | Deem et al. |
| 2007/0278103 A1 | 12/2007 | Hoerr et al. |
| 2007/0282302 A1 | 12/2007 | Wachsman et al. |
| 2007/0292411 A1 | 12/2007 | Salcedo et al. |
| 2007/0293782 A1 | 12/2007 | Marino |
| 2007/0299043 A1 | 12/2007 | Hunter et al. |
| 2008/0004673 A1 | 1/2008 | Rossing et al. |
| 2008/0009927 A1 | 1/2008 | Vilims |
| 2008/0015501 A1 | 1/2008 | Gertner |
| 2008/0021408 A1 | 1/2008 | Jacobsen et al. |
| 2008/0033049 A1 | 2/2008 | Mewshaw |
| 2008/0039746 A1 | 2/2008 | Hissong et al. |
| 2008/0039830 A1 | 2/2008 | Munger et al. |
| 2008/0051454 A1 | 2/2008 | Wang |
| 2008/0064957 A1 | 3/2008 | Spence |
| 2008/0071269 A1 | 3/2008 | Hilario et al. |
| 2008/0071306 A1 | 3/2008 | Gertner |
| 2008/0082050 A1 | 4/2008 | Solar et al. |
| 2008/0082109 A1 | 4/2008 | Moll et al. |
| 2008/0086072 A1 | 4/2008 | Bonutti et al. |
| 2008/0091193 A1 | 4/2008 | Kauphusman et al. |
| 2008/0097251 A1 | 4/2008 | Babaev |
| 2008/0097426 A1 | 4/2008 | Root et al. |
| 2008/0108867 A1 | 5/2008 | Zhou |
| 2008/0119879 A1 | 5/2008 | Brenneman et al. |
| 2008/0125772 A1 | 5/2008 | Stone et al. |
| 2008/0132450 A1 | 6/2008 | Lee et al. |
| 2008/0140002 A1 | 6/2008 | Ramzipoor et al. |
| 2008/0147002 A1 | 6/2008 | Gertner |
| 2008/0161662 A1 | 7/2008 | Golijanin et al. |
| 2008/0161717 A1 | 7/2008 | Gertner |
| 2008/0161801 A1 | 7/2008 | Steinke et al. |
| 2008/0171974 A1 | 7/2008 | Lafontaine et al. |
| 2008/0172035 A1 | 7/2008 | Starksen et al. |
| 2008/0172104 A1 | 7/2008 | Kieval et al. |
| 2008/0188912 A1 | 8/2008 | Stone et al. |
| 2008/0188913 A1 | 8/2008 | Stone et al. |
| 2008/0208162 A1 | 8/2008 | Joshi |
| 2008/0208169 A1 | 8/2008 | Boyle et al. |
| 2008/0213331 A1 | 9/2008 | Gelfand et al. |
| 2008/0215117 A1 | 9/2008 | Gross |
| 2008/0221448 A1 | 9/2008 | Khuri-Yakub et al. |
| 2008/0234790 A1 | 9/2008 | Bayer et al. |
| 2008/0243091 A1 | 10/2008 | Humphreys et al. |
| 2008/0245371 A1 | 10/2008 | Gruber |
| 2008/0249525 A1 | 10/2008 | Lee et al. |
| 2008/0249547 A1 | 10/2008 | Dunn |
| 2008/0255550 A1 | 10/2008 | Bell |
| 2008/0255642 A1 | 10/2008 | Zarins et al. |
| 2008/0262489 A1 | 10/2008 | Steinke |
| 2008/0275484 A1 | 11/2008 | Gertner |
| 2008/0281312 A1 | 11/2008 | Werneth et al. |
| 2008/0281347 A1 | 11/2008 | Gertner |
| 2008/0287786 A1 | 11/2008 | Lentz |
| 2008/0287918 A1 | 11/2008 | Rosenman et al. |
| 2008/0294037 A1 | 11/2008 | Richter |
| 2008/0300618 A1 | 12/2008 | Gertner |
| 2008/0312644 A1 | 12/2008 | Fourkas et al. |
| 2008/0312673 A1 | 12/2008 | Viswanathan et al. |
| 2008/0317818 A1 | 12/2008 | Griffith et al. |
| 2009/0018486 A1 | 1/2009 | Goren et al. |
| 2009/0018609 A1 | 1/2009 | DiLorenzo |
| 2009/0024194 A1 | 1/2009 | Arcot-Krishnamurthy et al. |
| 2009/0030312 A1 | 1/2009 | Hadjicostis |
| 2009/0036948 A1 | 2/2009 | Levin et al. |
| 2009/0043372 A1 | 2/2009 | Northrop et al. |
| 2009/0054082 A1 | 2/2009 | Kim et al. |
| 2009/0062873 A1 | 3/2009 | Wu et al. |
| 2009/0069671 A1 | 3/2009 | Anderson |
| 2009/0076409 A1 | 3/2009 | Wu et al. |
| 2009/0088735 A1 | 4/2009 | Abboud et al. |
| 2009/0105631 A1 | 4/2009 | Kieval |
| 2009/0112202 A1 | 4/2009 | Young |
| 2009/0118620 A1 | 5/2009 | Tgavalekos et al. |
| 2009/0118726 A1 | 5/2009 | Auth et al. |
| 2009/0125099 A1 | 5/2009 | Weber et al. |
| 2009/0131798 A1 | 5/2009 | Minar et al. |
| 2009/0143640 A1 | 6/2009 | Saadat et al. |
| 2009/0156988 A1 | 6/2009 | Ferren et al. |
| 2009/0157057 A1 | 6/2009 | Ferren et al. |
| 2009/0157161 A1 | 6/2009 | Desai et al. |
| 2009/0171333 A1 | 7/2009 | Hon |
| 2009/0192558 A1 | 7/2009 | Whitehurst et al. |
| 2009/0198223 A1 | 8/2009 | Thilwind et al. |
| 2009/0203962 A1 | 8/2009 | Miller et al. |
| 2009/0203993 A1 | 8/2009 | Mangat et al. |
| 2009/0204170 A1 | 8/2009 | Hastings et al. |
| 2009/0210953 A1 | 8/2009 | Moyer et al. |
| 2009/0216317 A1 | 8/2009 | Cromack et al. |
| 2009/0221955 A1 | 9/2009 | Babaev |
| 2009/0226429 A1 | 9/2009 | Salcedo et al. |
| 2009/0240249 A1 | 9/2009 | Chan et al. |
| 2009/0247933 A1 | 10/2009 | Maor et al. |
| 2009/0247966 A1 | 10/2009 | Gunn et al. |
| 2009/0248012 A1 | 10/2009 | Maor et al. |
| 2009/0253974 A1 | 10/2009 | Rahme |
| 2009/0264755 A1 | 10/2009 | Chen et al. |
| 2009/0270850 A1 | 10/2009 | Zhou et al. |
| 2009/0281533 A1 | 11/2009 | Ingle et al. |
| 2009/0287137 A1 | 11/2009 | Crowley |
| 2009/0318749 A1 | 12/2009 | Stolen et al. |
| 2010/0009267 A1 | 1/2010 | Chase et al. |
| 2010/0030061 A1 | 2/2010 | Canfield et al. |
| 2010/0048983 A1 | 2/2010 | Ball et al. |
| 2010/0049099 A1 | 2/2010 | Thapliyal et al. |
| 2010/0049186 A1 | 2/2010 | Ingle et al. |
| 2010/0049188 A1 | 2/2010 | Nelson et al. |
| 2010/0049191 A1 | 2/2010 | Habib et al. |
| 2010/0049283 A1 | 2/2010 | Johnson |
| 2010/0069837 A1 | 3/2010 | Rassat et al. |
| 2010/0076299 A1 | 3/2010 | Gustus et al. |
| 2010/0076425 A1 | 3/2010 | Carroux |
| 2010/0087782 A1 | 4/2010 | Ghaffari et al. |
| 2010/0106005 A1 | 4/2010 | Karczmar et al. |
| 2010/0114244 A1 | 5/2010 | Manda et al. |
| 2010/0130836 A1 | 5/2010 | Malchano et al. |
| 2010/0137860 A1 | 6/2010 | Demarais et al. |
| 2010/0137952 A1 | 6/2010 | Demarais et al. |
| 2010/0160903 A1 | 6/2010 | Krespi |
| 2010/0160906 A1 | 6/2010 | Jarrard |
| 2010/0168624 A1 | 7/2010 | Sliwa |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0191232 A1 | 7/2010 | Boveda |
| 2010/0217162 A1 | 8/2010 | Hissong et al. |
| 2010/0217234 A1 | 8/2010 | Grovender et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0228122 A1 | 9/2010 | Keenan et al. |
| 2010/0249604 A1 | 9/2010 | Hastings et al. |
| 2010/0249773 A1 | 9/2010 | Clark et al. |
| 2010/0256616 A1 | 10/2010 | Katoh et al. |
| 2010/0268217 A1 | 10/2010 | Habib |
| 2010/0268307 A1 | 10/2010 | Demarais et al. |
| 2010/0284927 A1 | 11/2010 | Lu et al. |
| 2010/0286684 A1 | 11/2010 | Hata et al. |
| 2010/0298821 A1 | 11/2010 | Garbagnati |
| 2010/0305036 A1 | 12/2010 | Barnes et al. |
| 2010/0312141 A1 | 12/2010 | Keast et al. |

(56) References Cited

U.S. PATENT DOCUMENTS

| | | |
|---|---|---|
| 2010/0324472 A1 | 12/2010 | Wulfman |
| 2011/0009750 A1 | 1/2011 | Taylor et al. |
| 2011/0021976 A1 | 1/2011 | Li et al. |
| 2011/0034832 A1 | 2/2011 | Cioanta et al. |
| 2011/0040324 A1 | 2/2011 | McCarthy et al. |
| 2011/0044942 A1 | 2/2011 | Puri et al. |
| 2011/0060324 A1 | 3/2011 | Wu et al. |
| 2011/0071400 A1 | 3/2011 | Hastings et al. |
| 2011/0071401 A1 | 3/2011 | Hastings et al. |
| 2011/0077498 A1 | 3/2011 | McDaniel |
| 2011/0092781 A1 | 4/2011 | Gertner |
| 2011/0092880 A1 | 4/2011 | Gertner |
| 2011/0104061 A1 | 5/2011 | Seward |
| 2011/0112400 A1 | 5/2011 | Emery et al. |
| 2011/0118600 A1 | 5/2011 | Gertner |
| 2011/0118726 A1 | 5/2011 | De La Rama et al. |
| 2011/0130708 A1 | 6/2011 | Perry et al. |
| 2011/0137155 A1 | 6/2011 | Weber et al. |
| 2011/0144479 A1 | 6/2011 | Hastings et al. |
| 2011/0146673 A1 | 6/2011 | Keast et al. |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0208096 A1 | 8/2011 | Demarais et al. |
| 2011/0257523 A1 | 10/2011 | Hastings et al. |
| 2011/0257564 A1 | 10/2011 | Demarais et al. |
| 2011/0257622 A1 | 10/2011 | Salahieh et al. |
| 2011/0257641 A1 | 10/2011 | Hastings et al. |
| 2011/0257642 A1 | 10/2011 | Griggs, III |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270238 A1 | 11/2011 | Rizq et al. |
| 2011/0306851 A1 | 12/2011 | Wang |
| 2011/0319809 A1 | 12/2011 | Smith |
| 2012/0029496 A1 | 2/2012 | Smith |
| 2012/0029500 A1 | 2/2012 | Jenson |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0029513 A1 | 2/2012 | Smith et al. |
| 2012/0059241 A1 | 3/2012 | Hastings et al. |
| 2012/0059286 A1 | 3/2012 | Hastings et al. |
| 2012/0059336 A1 | 3/2012 | Grovender et al. |
| 2012/0065506 A1 | 3/2012 | Smith |
| 2012/0065554 A1 | 3/2012 | Pikus |
| 2012/0095461 A1 | 4/2012 | Herscher et al. |
| 2012/0101413 A1 | 4/2012 | Beetel et al. |
| 2012/0101490 A1 | 4/2012 | Smith |
| 2012/0101538 A1 | 4/2012 | Ballakur et al. |
| 2012/0109021 A1 | 5/2012 | Hastings et al. |
| 2012/0116382 A1 | 5/2012 | Ku et al. |
| 2012/0116383 A1 | 5/2012 | Mauch et al. |
| 2012/0116392 A1 | 5/2012 | Willard |
| 2012/0116438 A1 | 5/2012 | Salahieh et al. |
| 2012/0116486 A1 | 5/2012 | Naga et al. |
| 2012/0123243 A1 | 5/2012 | Hastings |
| 2012/0123258 A1 | 5/2012 | Willard |
| 2012/0123261 A1 | 5/2012 | Jenson et al. |
| 2012/0123303 A1 | 5/2012 | Sogard et al. |
| 2012/0123406 A1 | 5/2012 | Edmunds et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130362 A1 | 5/2012 | Hastings et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136349 A1 | 5/2012 | Hastings |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0157992 A1 | 6/2012 | Smith et al. |
| 2012/0157993 A1 | 6/2012 | Jenson et al. |
| 2012/0158101 A1 | 6/2012 | Stone et al. |
| 2012/0158104 A1 | 6/2012 | Huynh et al. |
| 2012/0172837 A1 | 7/2012 | Demarais et al. |
| 2012/0172870 A1 | 7/2012 | Jenson et al. |
| 2012/0184952 A1 | 7/2012 | Jenson et al. |
| 2012/0197198 A1 | 8/2012 | Demarais et al. |
| 2012/0197252 A1 | 8/2012 | Deem et al. |
| 2012/0232409 A1 | 9/2012 | Stahmann et al. |
| 2012/0265066 A1 | 10/2012 | Crow et al. |
| 2012/0265198 A1 | 10/2012 | Crow et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0013024 A1 | 1/2013 | Levin et al. |
| 2013/0023865 A1 | 1/2013 | Steinke et al. |
| 2013/0035681 A1 | 2/2013 | Subramanaim et al. |
| 2013/0066316 A1 | 3/2013 | Steinke et al. |
| 2013/0085489 A1 | 4/2013 | Fain et al. |
| 2013/0090563 A1 | 4/2013 | Weber |
| 2013/0090578 A1 | 4/2013 | Smith et al. |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096550 A1 | 4/2013 | Hill |
| 2013/0096553 A1 | 4/2013 | Hill et al. |
| 2013/0096554 A1 | 4/2013 | Groff et al. |
| 2013/0096604 A1 | 4/2013 | Hanson et al. |
| 2013/0110106 A1 | 5/2013 | Richardson |
| 2013/0116687 A1 | 5/2013 | Willard |
| 2013/0165764 A1 | 6/2013 | Scheuermann et al. |
| 2013/0165844 A1 | 6/2013 | Shuros et al. |
| 2013/0165916 A1 | 6/2013 | Mathur et al. |
| 2013/0165917 A1 | 6/2013 | Mathur et al. |
| 2013/0165920 A1 | 6/2013 | Weber et al. |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0165926 A1 | 6/2013 | Mathur et al. |
| 2013/0165990 A1 | 6/2013 | Mathur et al. |
| 2013/0172815 A1 | 7/2013 | Perry et al. |
| 2013/0172872 A1 | 7/2013 | Subramaniam et al. |
| 2013/0172877 A1 | 7/2013 | Subramaniam et al. |
| 2013/0172878 A1 | 7/2013 | Smith |
| 2013/0172879 A1 | 7/2013 | Sutermeister |
| 2013/0172880 A1 | 7/2013 | Willard |
| 2013/0172881 A1 | 7/2013 | Hill et al. |

FOREIGN PATENT DOCUMENTS

| | | |
|---|---|---|
| EP | 1053720 A1 | 11/2000 |
| EP | 1084728 A1 | 3/2001 |
| EP | 1180004 A1 | 2/2002 |
| EP | 1335677 B1 | 8/2003 |
| EP | 1787673 A1 | 5/2004 |
| EP | 1461108 B1 | 9/2004 |
| EP | 1479409 A1 | 11/2004 |
| EP | 1874211 A2 | 1/2008 |
| EP | 1906853 A2 | 4/2008 |
| EP | 1961394 A2 | 8/2008 |
| EP | 1620156 B1 | 7/2009 |
| EP | 2076193 A2 | 7/2009 |
| EP | 2091455 A2 | 8/2009 |
| EP | 2197533 A1 | 6/2010 |

(56) References Cited

FOREIGN PATENT DOCUMENTS

| | | |
|---|---|---|
| EP | 2208506 A1 | 7/2010 |
| EP | 1579889 B1 | 8/2010 |
| EP | 2092957 B1 | 1/2011 |
| EP | 2349044 A1 | 8/2011 |
| EP | 2027882 B1 | 10/2011 |
| EP | 2378956 A2 | 10/2011 |
| EP | 2037840 B1 | 12/2011 |
| EP | 2204134 B1 | 4/2012 |
| EP | 2450010 | 5/2012 |
| EP | 2320821 B1 | 10/2012 |
| GB | 2456301 A | 7/2009 |
| JP | 6277296 A | 10/1994 |
| JP | 8257128 A | 10/1996 |
| JP | 2000116788 A | 4/2000 |
| JP | 2001095924 A | 4/2001 |
| JP | 2001333984 A | 12/2001 |
| JP | 2002536032 A | 10/2002 |
| WF | 2004100813 A2 | 11/2004 |
| WO | 9207610 A1 | 5/1992 |
| WO | 9217236 A1 | 10/1992 |
| WO | 9222345 A1 | 12/1992 |
| WO | 9318816 A1 | 9/1993 |
| WO | 9320882 A1 | 10/1993 |
| WO | 9402194 A1 | 2/1994 |
| WO | 9403213 A2 | 2/1994 |
| WO | 9404216 A1 | 3/1994 |
| WO | 9640349 | 12/1996 |
| WO | 9839056 | 9/1998 |
| WO | 9858588 A1 | 12/1998 |
| WO | 9900060 A1 | 1/1999 |
| WO | 0024451 A2 | 5/2000 |
| WO | 0047118 A1 | 8/2000 |
| WO | 0170323 A1 | 9/2001 |
| WO | 03026525 A1 | 4/2003 |
| WO | 2004047899 A1 | 6/2004 |
| WO | 2004110258 A2 | 12/2004 |
| WO | 2006007137 A1 | 1/2006 |
| WO | 2006105121 A2 | 10/2006 |
| WO | 2006113912 A1 | 10/2006 |
| WO | 2008014465 A2 | 1/2008 |
| WO | 2009121017 A1 | 10/2009 |
| WO | 2010067360 A2 | 6/2010 |
| WO | 2010102310 A2 | 9/2010 |
| WO | 2011005901 A2 | 1/2011 |
| WO | 2011011765 A2 | 1/2011 |
| WO | 2011053757 A1 | 5/2011 |
| WO | 2011053772 A1 | 5/2011 |
| WO | 2011091069 A1 | 7/2011 |
| WO | 2011130534 A2 | 10/2011 |
| WO | 2012019156 A1 | 2/2012 |
| WO | 2013049601 A2 | 4/2013 |

OTHER PUBLICATIONS

Terumo Corporation Product Sheet, "Heartrail II PTCA Guiding Catheters," dated before Feb. 20, 2009, one sheet.
Terumo Corporation Product Sheet, "Crosswire/Crosswire NT," dated before Feb. 20, 2009, one sheet.
Terumo Corporation Product Sheet, "Runthrough NS PTCA Guide Wire," dated before Feb. 20, 2009, one sheet.
Terumo Corporation Product Sheet, "Ryujin Plus PTCA Dilatation Catheters," dated before Feb. 20, 2009, one sheet.
Terumo Corporation Product Sheet, "Tsunami Coronary Stent," dated before Feb. 20, 2009, one sheet.
CardioVascular Technologies Inc., "Heated Balloon Device Technology," 11 pages, 2008.
Strategic Business Development, Inc., "Thermal and Disruptive Angioplasty: A Physician's Guide," 8 pages, 1990.
Zhang et al., "Non-contact Radio-Frequency Ablation for Obtaining Deeper Lesions," IEEE Transaction on Biomedical Engineering, vol. 50, No. 2, 6 pages, Feb. 2003.
Lazebnik et al., "Tissue Strain Analytics Virtual Touch Tissue Imaging and Qualification," Siemens Whitepaper, Oct. 2008, 7 pages.
Han et al., "Third-Generation Cryosurgery for Primary and Recurrent Prostate Caner," BJU International, vol. 93, pp. 14-18.
Zhou et al., "Mechanism Research of Cryoanalgesia," Forefront Publishing Group, 1995.
Florete, "Cryoblative Procedure for Back Pain," Jacksonville Medicine, Oct. 1998, 10 pages.
Stevenson, "Irrigated RF Ablation: Power Titration and Fluid Management for Optimal Safety Efficacy," 2005, 4 pages.
Giliatt et al., "The Cause of Nerve Damage in Acute Compression," Trans Am Neurol Assoc, 1974: 99; 71-4.
Omura et al., "A Mild Acute Compression Induces Neurapraxia in Rat Sciatic Nerve," The International Journal of Neuroscience, vol. 114 (12), pp. 1561-1572.
Baun, "Interaction with Soft Tissue," Principles of General & Vascular Sonography, Chapter 2, pp. 23-24, Before Mar. 2012.
Blue Cross Blue Shield Medicaly Policy, "Surgery Section—MRI-Guided Focused Ultrasound (MRgFUS) for the Treatment of Uterine Fibroids and Other Tumors," 2005, 5 pages.
Gentry et al., "Combines 3D Intracardiac Echo and Ultrasound Ablation," Medical Imaging 2003: Ultrasonic and Signal Processing, vol. 5035, 2003, pp. 166-173.
Lafon et al., "Optmizing the Shape of Ultrasound Transducers for Interstitial Thermal Ablations," MEd Phys. Mar. 2002; 29(3): 290-7 (abstract only).
G. Ter Haar, "Ultrasound Focal Beam Surgery," Ultrasound in Med. & Biol., 1995, vol. 21, No. 9, pp. 1089-1100.
Seip et al., "Transurethral High Intensity Focused Ultrasound: Catheter Based Prototypes and Experimental Results," IEEE Ultrasonics Symposium Proceeding, 2000, 4 pages.
Toytman et al., "Tissue Dissection with Ultrafast Laser Using Extended and Multiple Foci," SPIE Proceeding, Optical Interactions with Tissues and Cells XXI, vol. 7562, 2010, 10 pages.
Zhoue et al., "Non-Thermal Ablation of Rabbit Liver VX2 Tumore by Pulsed High Intensity Focused Ultrasound Contrast Agent: Pathological Characteristics," World Journal of Gastroenterology, vol. 14(43), Nov. 21, 2008, pp. 6743-6747.
Van Den Berg, "Light echoes image the human body," OLE, Oct. 2001, p. 35-37.
"IntraLuminal: Products," IntraLuminal Therapeutics, Inc., 2003, p. 1-9.
"Laser Catheter to Aid Coronary Surgery," TechTalk: MIT, Jan. 9, 1991, p. 1-4.
"Optical Coherence Tomography: Advantages of OCT," LightLab Imaging Technology.
"Optical Coherence Tomography: Image Gallery Cardiovascular Procedures," LightLab Imaging Technology.
"Optical Coherence Tomography: LightLab Imaging Starts US Cardiology Clinical Investigations," LightLab Imaging Technology, 2002.
"Optical Coherence Tomography: LightLab Sees Bright Prospects for Cardiac Application of OCT Technology," LightLab Imaging Technology, 2001, vol. 27, No. 35.
"Optical Coherence Tomography: What is OCT?," LightLab Imaging Technology.
"Optical Coherence Tomography: Why Use OCT?," LightLab Imaging Technology.
"Products—Functional Measurement," VOLCANO Functional Measurement Products US, Mar. 24, 2003, p. 1-2.
Brown et al., "Radiofrequency capacitive heaters: the effect of coupling medium resistivity on power absorption along a mouse leg," Physics in Medicine and Biology, 1993, p. 1-12, vol. 38.
Carrington, "Future of CVI: It's all about plaque: Identification of vulnerable lesions, not 'rusty pipes,' could become cornerstone of preventive cardiology," Diagnostic Imaging, 2001, p. 1-8.
Chen et al., "Percutaneous pulmonary artery denervation completely abolishes experimental pulmonary arterial hypertension in vivo," EuroIntervention, 2013, p. 1-8.
Cimino, "Preventing plaque attack," Mass High Tech, 2001, p. 1-2.
Dahm et al., "Relation of Degree of Laser Debulking of In-Stent Restenosis as a Predictor of Restenosis Rate," The American Journal of Cardiology, 2002, p. 68-70, vol. 90.

(56) References Cited

OTHER PUBLICATIONS

De Korte et al., "Characterization of Plaque Components With Intravascular Ultrasound Elastography in Human Femoral and Coronary Arteries In Vitro," Circulation, Aug. 8, 2000, p. 617-623.
Durney et al., "Radiofrequency Radiation Dosimetry Handbook," Oct. 1986, p. 1-2, Fourth Edition.
Durney et al., "Radiofrequency Radiation Dosimetry Handbook: Contents," Oct. 1986, p. 1-5, Fourth Edition.
Fournier-Desseux et al., "Assessment of 1-lead and 2-lead electrode patterns in electrical impedance endotomography," Physiological Measurement, 2005, p. 337-349. Vo. 26, Institute of Physics Publishing.
Fram et al., "Feasibility of Radiofrequency Powered, Thermal Balloon Ablation of Atrioventricular Bypass Tracts via the Coronary Sinus: In Vivo Canine Studies," PACE, Aug. 1995, p. 1518-1530, vol. 18.
Fram et al., "Low Pressure Radiofrequency Balloon Angioplasty: Evaluation in Porcine Peripheral Arteries," JACC, 1993, p. 1512-1521, vol. 21, No. 6, American College of Cardiology.
Fujimori et al., "Significant Prevention of In-Stent Restenosis by Evans Blue in Patients with Acute Myocardial Infarction," American Heart Association, 2002.
Fujita et al., "Sarpogrelate, An Antagonist of 5-HT(2A) Receptor, Treatment Reduces Restenosis After Coronary Stenting," American Heart Association, 2002.
Gabriel, "Appendix A: Experimental Data," 1999, p. 1-21.
Gabriel, "Appendix C: Modeling the frequency dependence of the dielectric properties to a 4 dispersions spectrum," p. 1-6.
Gregory et al., "Liquid Core Light Guide for Laser Angioplasty," The Journal of Quantum Electronics, Dec. 1990, p. 2289-2296, vol. 26, No. 12.
Kaplan et al., "Healing after Arterial Dilatation with Radiofrequency Thermal and Nonthermal Balloon Angioplasty Sytems," Journal of Investigative Surgery, 1993, p. 33-52, vol. 6.
Kolata, "New Studies Question Value of Opening Arteries," The New York Times, Mar. 21, 2004, p. 1-5.
Konings et al., "Development of an Intravascular Impedance Catheter for Detection of Fatty Lesions in Arteries," IEEE Transactions on Medical Imaging, Aug. 1997, p. 439-446, vol. 16, No. 4.
Kurtz et al., "Lamellar Refractive Surgery with Scanned Intrastromal Picosecond and Femtosecond Laser Pulses in Animal Eyes," Journal of Refractive Surgery, Sep./Oct. 1998, p. 541-548.
Lee et al., "Thermal Compression and Molding of Atherosclerotic Vascular Tissue With Use of Radiofrequency Energy: Implications for Radiofrequency Balloon Angioplasty," JACC, 1989, p. 1167-1175, vol. 13, No. 5, American College of Cardiology.
Lima et al., "Efficacy and Safety of Oral Sirolimus to Treat and Prevent In-Stent Restenosis: A Pilot Study Results," American Heart Association, 2002, p. 2929.
Lima et al., "Systemic Immunosuppression Inhibits In-Stent Coronary Intimal Proliferation in Renal Transplant Patients," American Heart Association, 2002, p. 2928.
Morice et al., "A Randomized Comparison of a Sirolimus-Eluting Stent With a Standard Stent for Coronary Revascularization," The New England Journal of Medicine, Jun. 6, 2012, p. 1773-1780, vol. 346, No. 23.
Muller-Leisse et al., "Effectiveness and Safety of Ultrasonic Atherosclerotic Plaque Ablation: In Vitro Investigation," CardioVascular and Interventional Radiology, 1993, p. 303-307, vol. 16.
Nair et al., "Regularized Autoregressive Analysis of Intravascular Ultrasound Backscatter: Improvement in Spatial Accuracy of Tissue Maps," IEEE Transactions on Ultrasonics, Apr. 2004, p. 420-431, vol. 51, No. 4.
Popma et al., "Percutaneous Coronary and Valvular Intervention," p. 1364-1405.
Resar et al., "Endoluminal Sealing of Vascular Wall Disruptions With Radiofrequency-Heated Balloon Angioplasty," Catheterization and Cardiovascular Diagnosis, 1993, p. 161-167, vol. 29.
Romer et al., "Histopathology of Human Coronary Atherosclerosis by Quantifying Its Chemical Composition With Raman Spectroscopy," Circulation, 1998, p. 878-885, vol. 97.
Schauerte et al., "Catheter Ablation of Cardiac Autonomic Nerves for Prevention of Vagal Atrial Fibrillation," Circulation, 2000, p. 2774-2780, vol. 102.
Scheller et al., "Intracoronary Paclitaxel Added to Contrast Media Inhibits In-Stent Restenosis of Porcine Coronary Arteries," American Heart Association, 2002, p. 2227.
Scheller et al., "Potential solutions to the current problem: coated balloon," EuroIntervention, 2008, p. C63-C66, vol. 4 (Supplement C).
Shaffer, "Scientific basis of laser energy," Clinics in Sports Medicine, 2002, p. 585-598, vol. 21.
Shmatukha et al., "MRI temperature mapping during thermal balloon angioplasty," Physics in Medicine and Biology, 2006, p. N163-N171, vol. 51.
Slager et al., "Vaporization of Atherosclerotic Plaques by Spark Erosion," J Am Coll Cardiol, 1985, p. 21-25.
Stiles et al., "Simulated Characterization of Atherosclerotic Lesions in the Coronary Arteries by Measurement of Bioimpedance," IEEE Transactions on Biomedical Engineering, Jul. 2003, p. 916-921, vol. 50, No. 7.
Suselbeck et al., "In vivo intravascular electric impedance spectroscopy using a new catheter with integrated microelectrodes," Basic Res Cardiol, 2005, p. 28-34, vol. 100.
Suselbeck et al., "Intravascular electric impedance spectroscopy of atherosclerotic lesions using a new impedance catheter system," Basic Res Cardiol, 2005, p. 446-452, vol. 100.
Tepe et al., "Local Delivery of Paclitaxel to Inhibit Restenosis during Angioplasty of the Leg," The New England Journal of Medicine, 2008, p. 689-699, vol. 358.
US 8,398,630, 03/2013, Demarais et al. (withdrawn)

\* cited by examiner

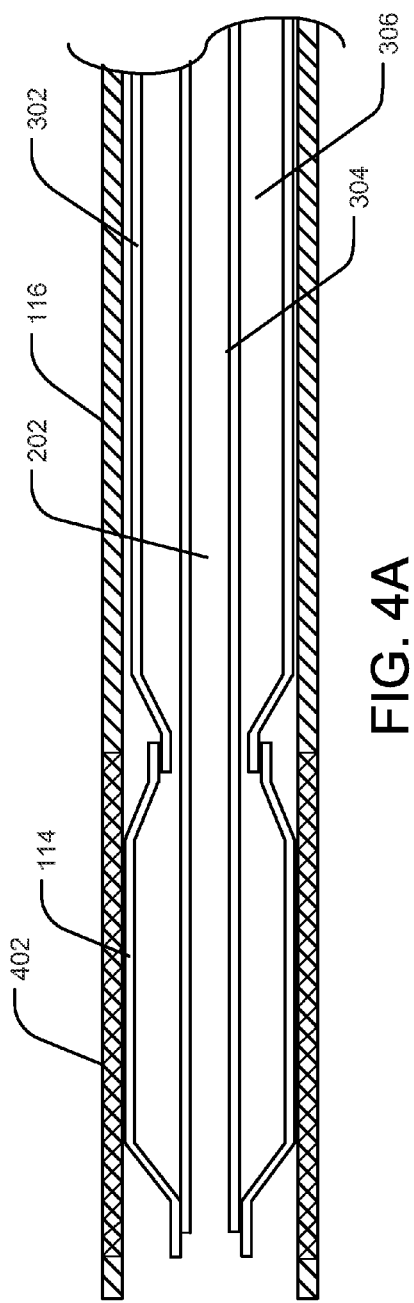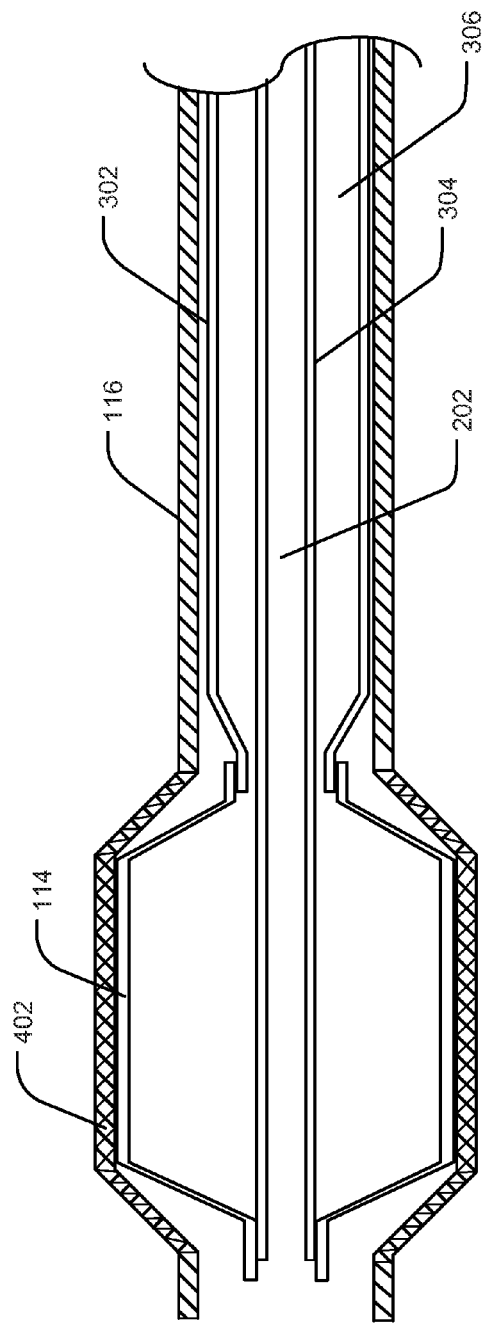

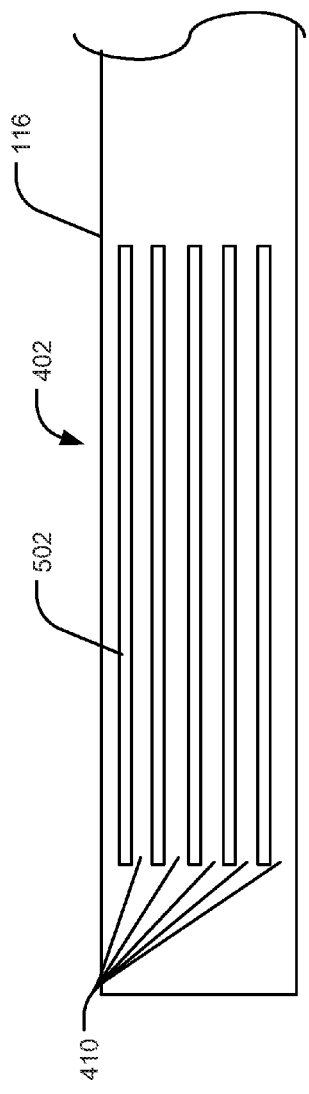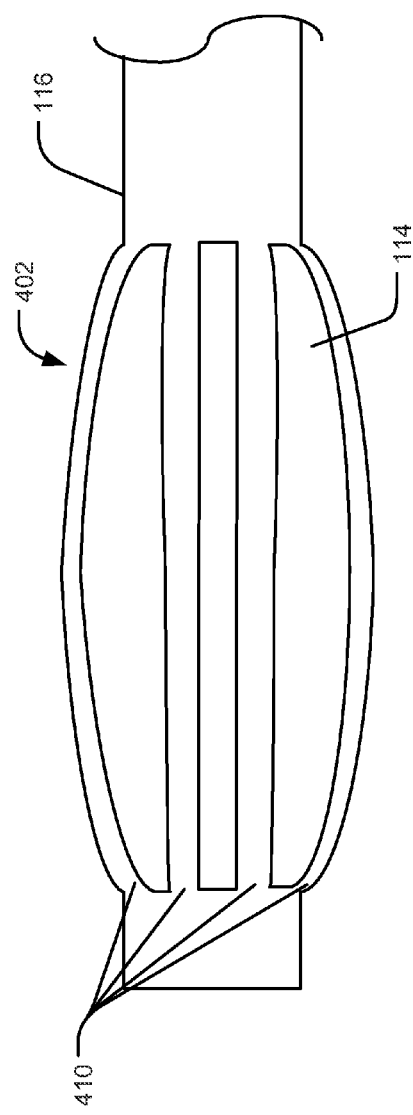
FIG. 5A
FIG. 5B

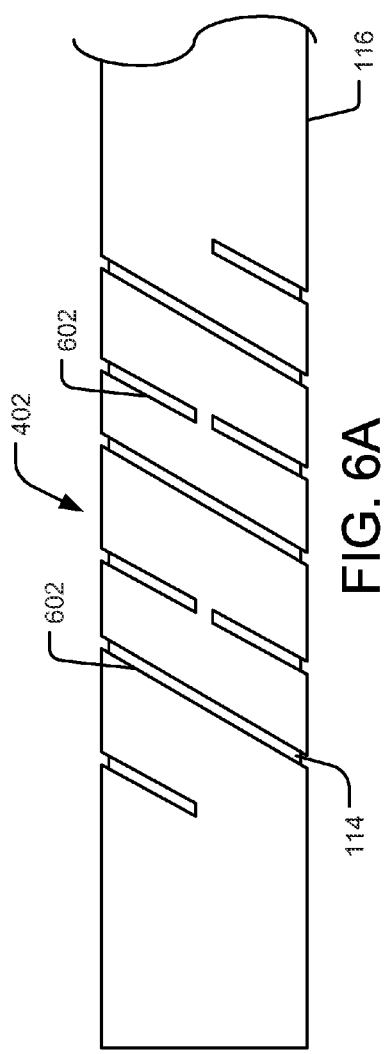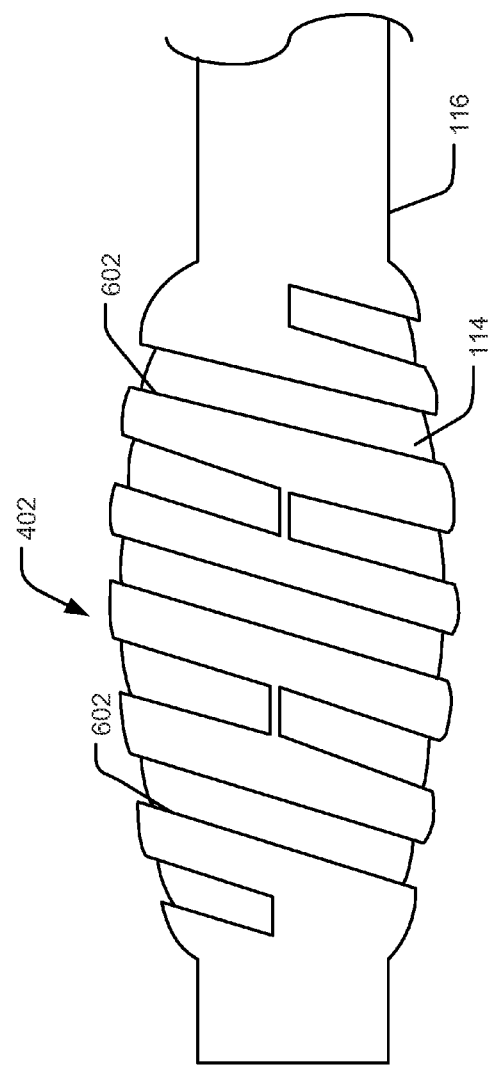

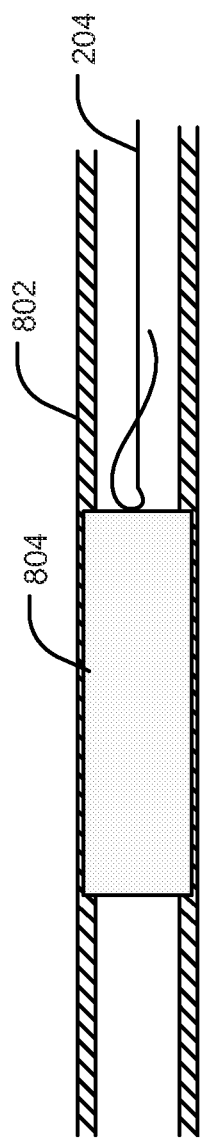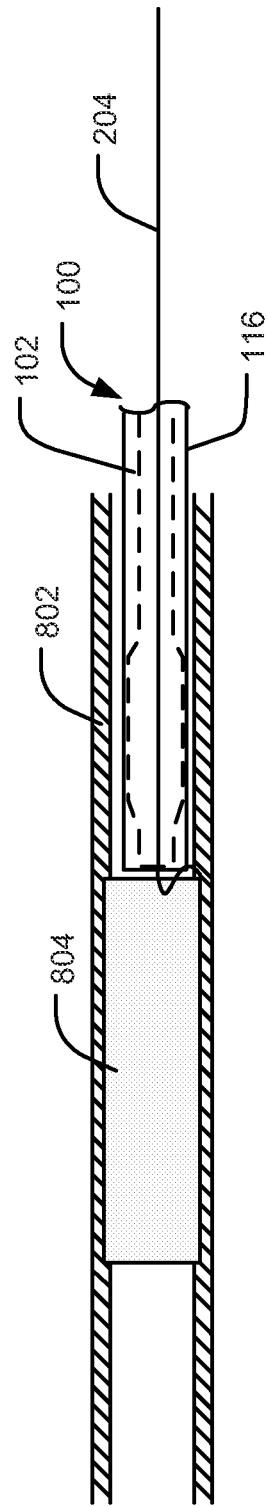
FIG. 8A
FIG. 8B

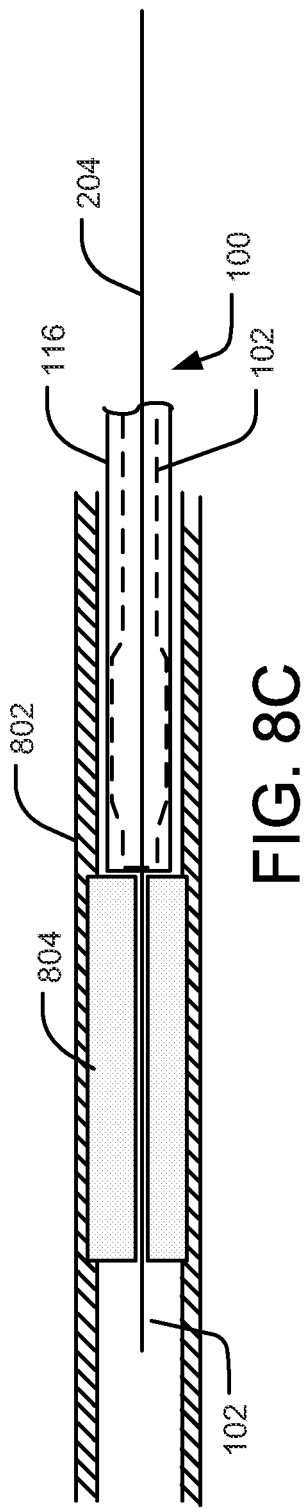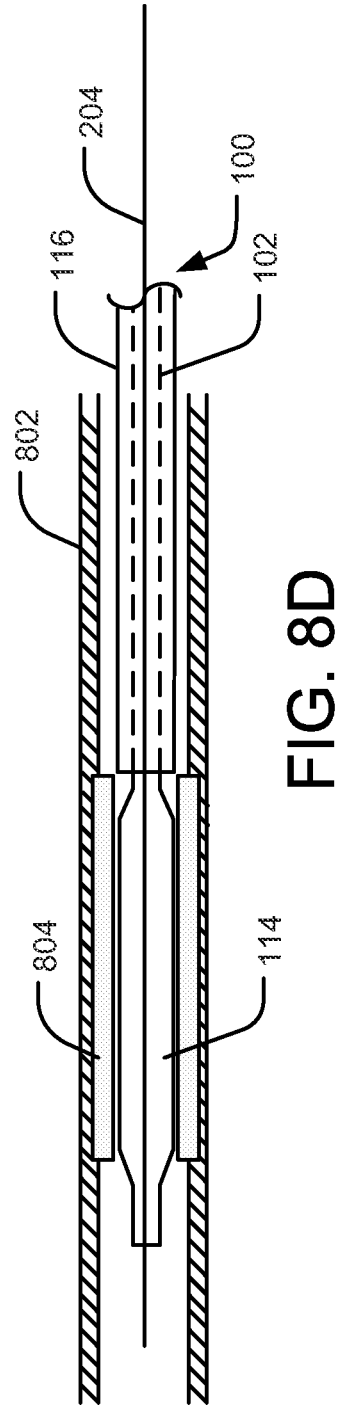

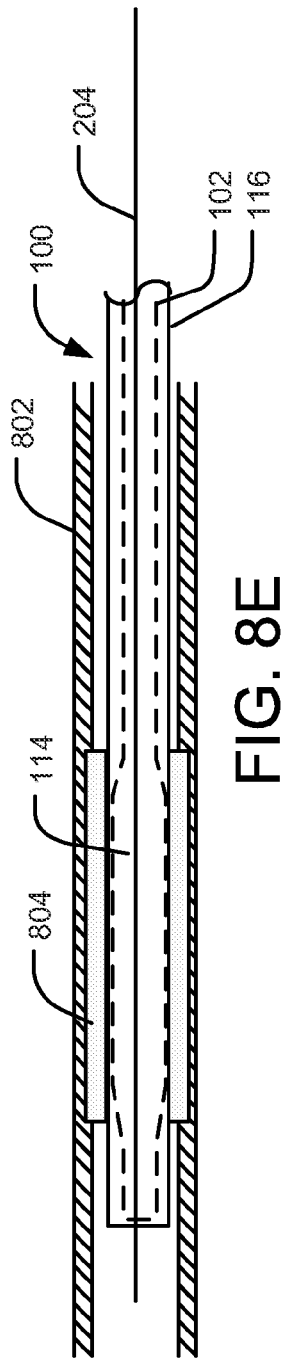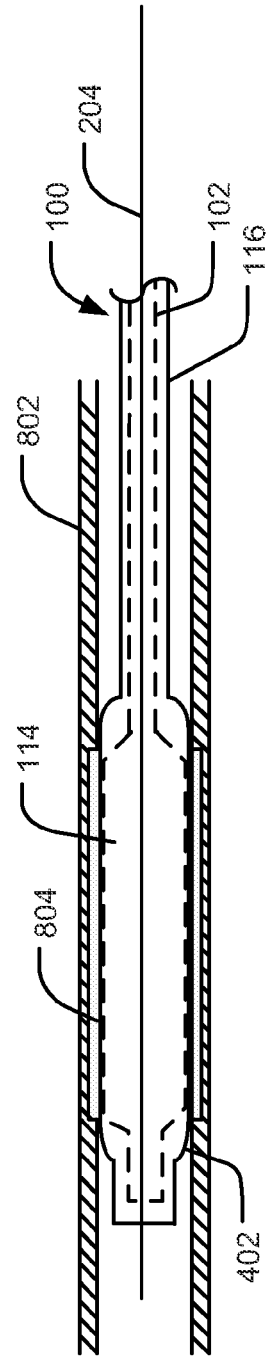

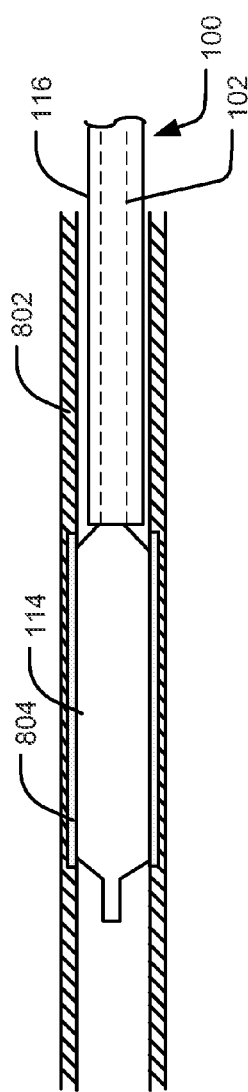
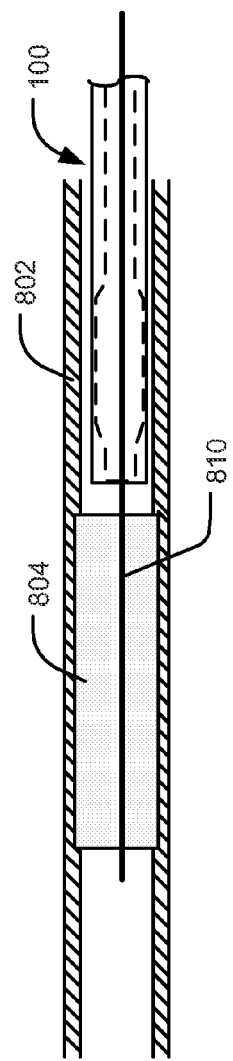

INTEGRATED CROSSING BALLOON CATHETER

CROSS-REFERENCE TO RELATED APPLICATIONS

This application claims priority under 35 U.S.C. §119 to U.S. Provisional Application Ser. No. 61/548,629, filed Oct. 18, 2011, the entirety of which is incorporated herein by reference.

TECHNICAL FIELD

This disclosure relates generally to catheters and more particularly to integrated intravascular catheters for crossing chronic total occlusions.

BACKGROUND

The use of intravascular catheters is an effective method for treating many types of vascular disease. In general, an intravascular catheter is inserted into the vascular system of a patient and navigated through the vasculature to a desired target site. Using this method, virtually any target site in the patient's vascular system may be accessed, including the coronary, cerebral, and peripheral vasculature. Example therapeutic applications of intravascular catheters include percutaneous transluminal angioplasty (PTA), and percutaneous transluminal coronary angioplasty (PTCA).

Intravascular catheters are commonly used in conjunction with a guidewire. A guidewire may be advanced through the patient's vasculature until it reaches a target location. Once in place, the catheter may be threaded onto the guidewire and urged distally until the distal end of the catheter reaches the target location.

Typically, the guidewire is inserted into the patient's vasculature from a convenient percutaneous location and then advanced to a target region. The path traversed by the catheter through the vascular system is often tortuous, requiring the guidewire to change direction frequently. To conform to a patient's circuitous vascular system, the guidewire is preferably flexible, particularly near the distal end.

During its course through the vasculature, the guidewire may confront a stenosis, lesion, or clot. Sometimes, the stenosis completely blocks the vessel, as is the case with a chronic total occlusion (CTO). In these cases, the guidewire may not be able to penetrate the occlusion, owing to its flexibility. To overcome this difficulty, a catheter can be inserted over the guidewire to increase rigidity, or a more rigid guidewire may replace the existing guidewire.

If the occlusion is hard plaque, even the catheter and guidewire combination may not be able to cross it. In these cases, the intravascular catheter may be replaced by a crossing catheter. A crossing catheter may be configured to advance through the occlusion. For example, the crossing catheter may include a vibrating distal portion, a smaller profile than the intravascular catheter, a rigid distal portion, and/or a tapered distal tip enabling it to penetrate through hard plaques relatively easily. Once the plaque is crossed, the crossing catheter is removed and replaced by a balloon catheter to enlarge the pathway through the occlusion and/or positions a stent across the occlusion.

In this described arrangement, once the occlusion is crossed, the crossing catheter is retracted, and the balloon catheter is inserted in its place. Retraction and replacement, however, increases operation time and cost. Moreover, sometimes, the pathway formed through the plaque may not be sufficient to insert the flexible balloon catheter, increasing placement complexity.

Therefore, there exists a need for an integrated medical device that can penetrate the occlusion and without complete retraction provide interventional treatment (for example, but not limited to, dilating the occlusion or placing a stent) at the target location.

SUMMARY

Some embodiments of the present disclosure pertain to integrated crossing and balloon catheters, as well as related components, systems and methods. Some embodiments provide for alternative structures, methods of making, and methods of using the integrated crossing and balloon catheter. In many instances, it may be desirable to penetrate and remove chronic total occlusions in a patient's vasculature. Stents, dilatation balloons, or atherectomy devices may be inserted in the occlusion to alleviate stenosis. Some embodiments of the present disclosure introduce a novel catheter that integrates the features of a crossing, scoring and/or balloon catheter in one medical device.

In one embodiment, the integrated catheter includes a catheter shaft having a proximal end, a distal end, a proximal end portion proximate the proximal end and a distal end portion proximate the distal end. The catheter further includes a hub assembly secured to the proximal end of the catheter shaft, and an inflatable balloon secured to the distal end of the catheter shaft. Further, a stiffening tube may be positioned over the inflatable balloon and the distal end portion of the catheter shaft. The stiffening tube may be configured to advance through a vasculature with the catheter shaft as a unit. Moreover, the stiffening tube may be translatable along the catheter shaft from a first position in which the inflatable balloon is within the stiffening tube to a second position in which the inflatable balloon is exposed from the stiffening tube.

In other embodiments, the length of the stiffening tube may be less than the length of the catheter shaft. For example, the stiffening tube may extend along approximately 70% or more of the catheter shaft length. Further, the stiffening tube may be translatable relative to the catheter shaft over a distance at least as long as the length of the inflatable balloon, so that in one position it covers the balloon and in another position it exposes the balloon.

In another embodiment, the stiffening tube may be dimensioned such that its proximal portion remains exterior of a patient while the balloon is positioned proximate a target site within a vessel lumen. Moreover, in some embodiments the proximal end of the stiffening tube may flare outwards allowing a physician to grasp the tube and manipulate it.

In other embodiments, the stiffening tube may frictionally engage the catheter shaft when the stiffening tube is translated along the catheter shaft.

The present disclosure further describes a crossing catheter system including a catheter having an elongate shaft extending from a hub assembly at a proximal end of the catheter to an inflatable balloon at a distal end of the catheter. The catheter further includes an inflation lumen extending through the elongate shaft from the hub assembly to the inflatable balloon for delivering inflation fluid to the inflatable balloon. The system further includes a stiffening tube having a proximal end, a distal end, and a length measured from the proximal end to the distal end. The stiffening tube surrounds the elongate shaft and is in intimate contact with an outer surface of the elongate shaft along a majority of the length of the elongate shaft. Further, the stiffening tube may be configured to advance through a vasculature with the catheter as a unit. In addition, the stiffening tube may be translatable along the elongate shaft from a first position in which a distal end of the stiffening tube is positioned distal of the inflatable balloon to a second position in which the distal end of the stiffening tube is positioned proximal of the inflatable balloon.

In other embodiments, the stiffening tube may have a tapered distal tip configured to expand from a first configuration to a second configuration. The first configuration is a low profile configuration for traversing an occlusion and the second configuration is sized to allow the inflatable balloon to be deployed through the tapered distal tip. Further, the stiffening tube may include an expandable region surrounding the inflatable balloon. The expandable region may include a distensible material configured to expand radially outward when the inflatable balloon is inflated within the expandable region. In some embodiments, the expandable region may include a plurality of slots.

The present disclosure further describes methods for crossing an occlusion in a vessel lumen. In some embodiments, the method includes advancing a crossing balloon catheter over a guidewire intravascularly to a location proximal of an occlusion in the vessel lumen. The crossing balloon catheter may include an elongate shaft extending between an inflatable balloon and a hub assembly, and a stiffening tube surrounding the balloon and extending proximal of the balloon over a majority of a length of the elongate shaft. The method further includes positioning the balloon across the occlusion, and retracting the stiffening tube from the balloon by translating the tube proximally relative to the elongate shaft. Further, the method includes inflating the balloon within the occlusion to expand the occlusion by delivering inflation fluid through an inflation lumen of the elongate shaft from the hub assembly to the balloon.

In some embodiments, the balloon may be positioned across the occlusion with the stiffening tube surrounding the inflatable balloon. Further, the balloon may be at least partially inflated within the stiffening tube while positioning the balloon across the occlusion.

The foregoing and other objects, aspects, features, and advantages of the present disclosure will become apparent from the following description, the drawings, and from the claims.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIGS. 4A and 4B are illustrative diagrams of an alternative embodiment of the crossing balloon catheter with the balloon in a deflated and inflated position, respectively.

FIGS. 5A and 5B are illustrative diagrams of an alternative embodiment of the crossing balloon catheter with the balloon in a deflated and inflated position, respectively.

FIGS. 6A and 6B are illustrative diagrams of an alternative embodiment of the crossing balloon catheter with the balloon in a deflated and inflated position, respectively.

FIGS. 8A-8H illustrate various aspects for crossing an occlusion using the crossing balloon catheter of FIG. 1.

DETAILED DESCRIPTION

Reference will now be made in detail to some example embodiments of the present disclosure, an example of which is illustrated in the accompanying drawings. Wherever possible, the same reference numbers will be used throughout the drawings to refer to the same or like parts.

Overview

Some embodiments of the present disclosure introduce an integrated crossing intravascular catheter to cross an occlusion in a patient's vasculature, dilate the occlusion, and/or provide therapeutic treatment at the occlusion site without exchanging medical devices. This integrated catheter performs the functions of both a crossing catheter and an intravascular catheter, such as a balloon catheter. To this end, a stiffening tube may cover and be integrated with the intravascular catheter, such that the stiffening tube may be translatable along the length of the intravascular catheter. In one position, the stiffening tube may cover a distal portion of the intravascular catheter, providing stiffness and support to cross the occlusion, and in a second position, the stiffening tube may expose the distal portion of the intravascular catheter, to provide therapeutic treatment to the occlusion.

The intravascular catheter, in the following sections, is embodied as a balloon catheter. It will be understood that this choice is merely exemplary and any other intravascular catheter may replace the balloon catheter without departing from the scope of the present disclosure.

For purposes of this disclosure, "proximal" refers to the end closer to the device operator during use, and "distal" refers to the end further from the device operator during use.

Exemplary Device Embodiments

Figure 1A:
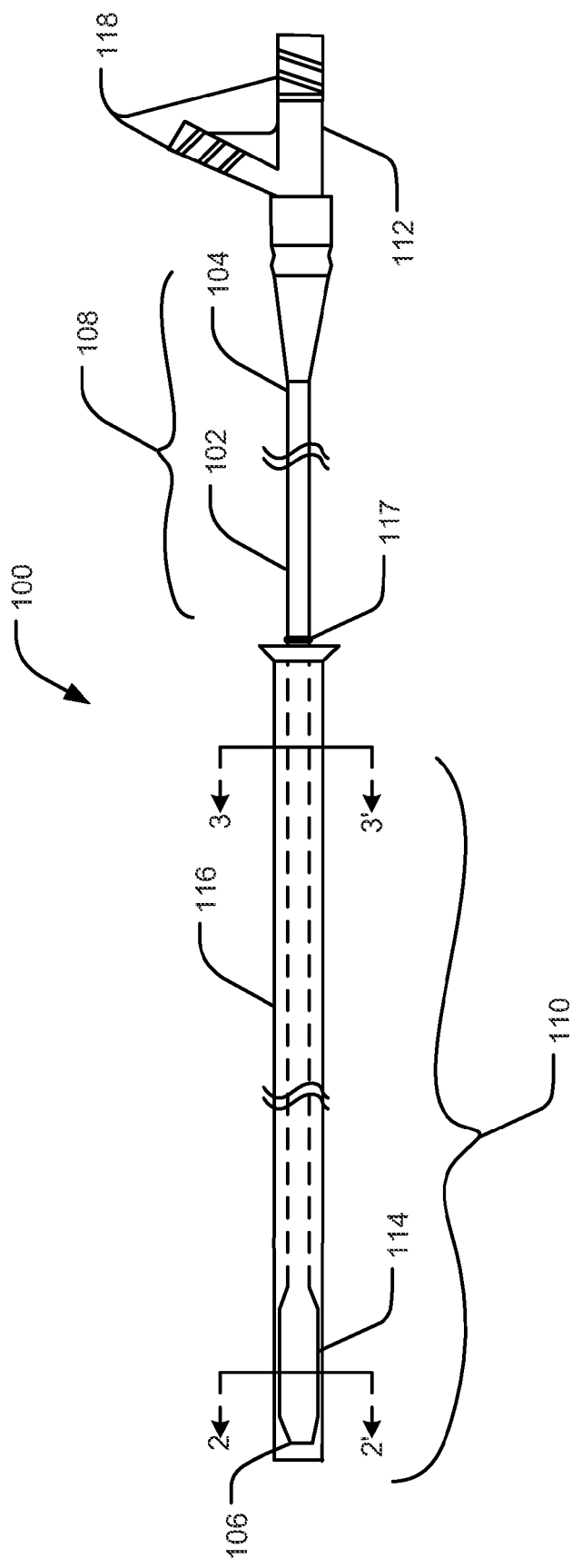
FIG. 1A is an illustrative diagram of a crossing balloon catheter in a first position according to one embodiment of the present disclosure.
Figure 1B:
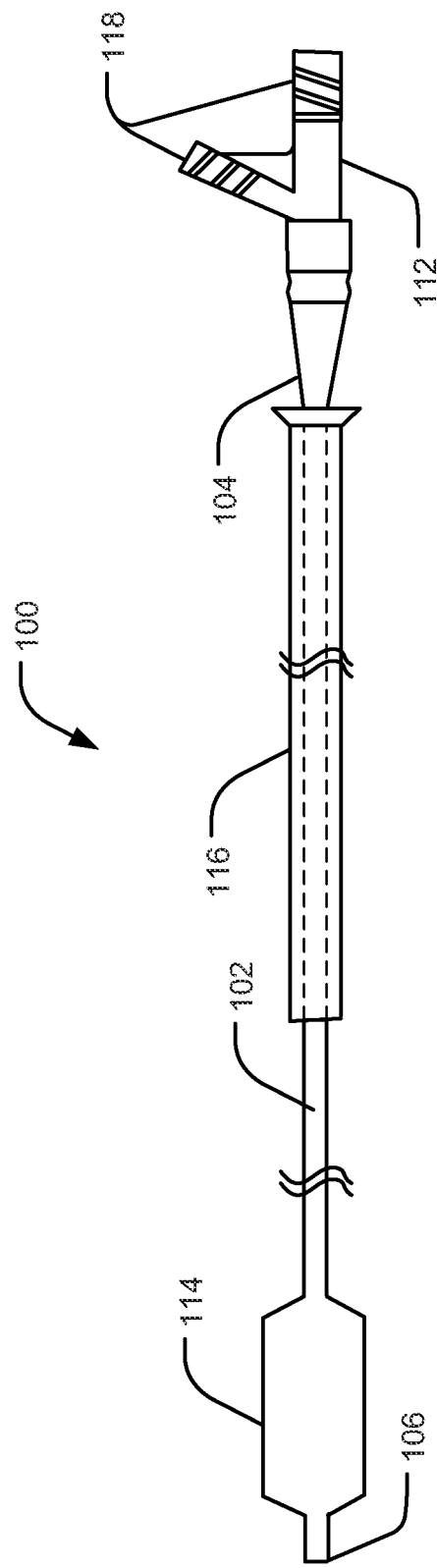
FIG. 1B is an illustrative diagram of the crossing balloon catheter of FIG. 1A in a second position according to one embodiment of the present disclosure.
Figure 2:
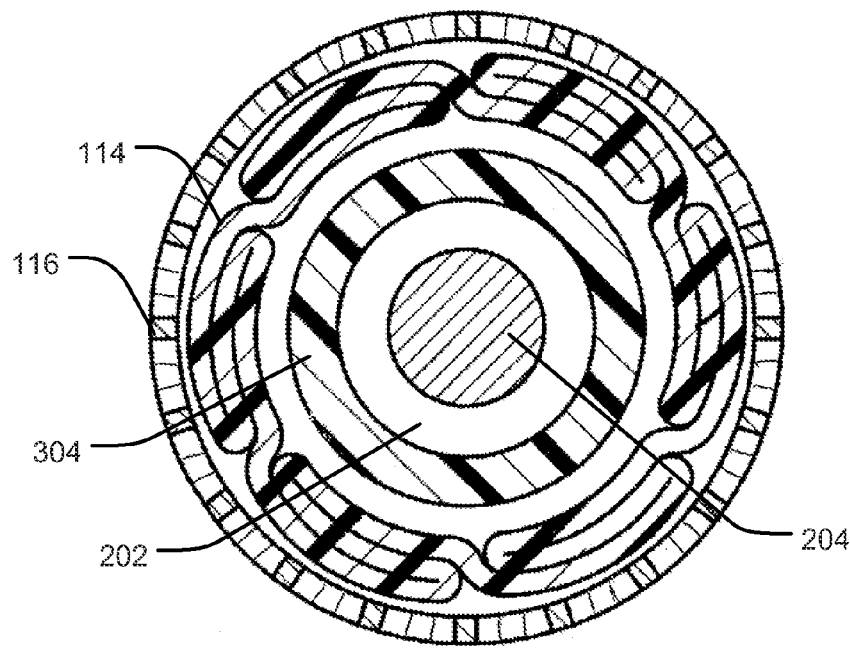
FIG. 2 is a cut-away sectional view of the crossing balloon catheter of FIG. 1 taken along line 2-2'.
Figure 3:
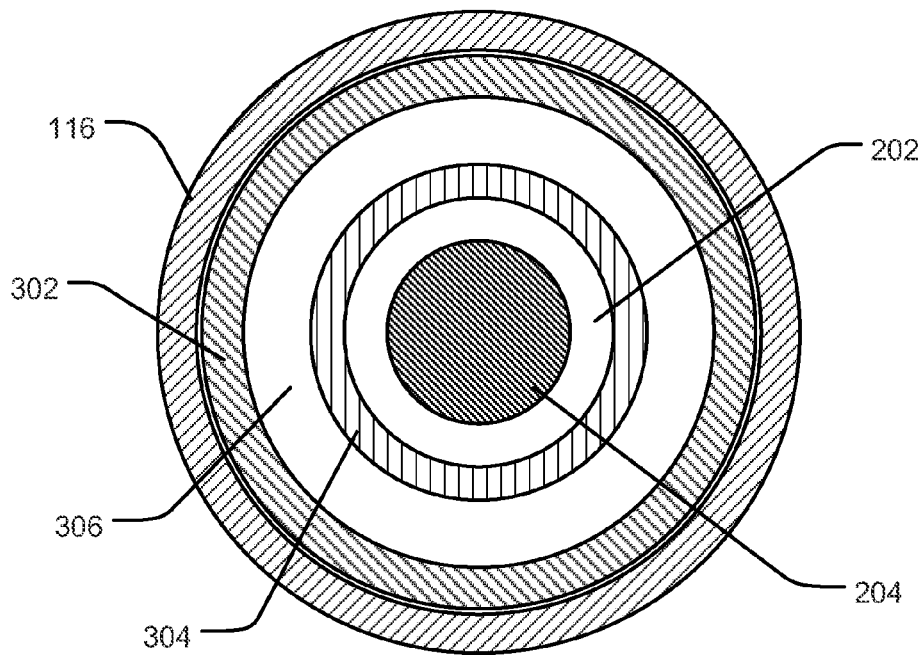
FIG. 3 is a cut-away sectional view of the crossing balloon catheter of FIG. 1 taken along line 3-3'.

FIGS. 1-3 illustrate an exemplary integrated crossing balloon catheter 100. More particularly, FIG. 1A depicts the crossing balloon catheter 100 in a first position and FIG. 1B depicts the crossing balloon catheter 100 in a second position, while FIGS. 2 and 3 are cross-sectional views of the catheter 100 taken along line 2-2' and line 3-3' in FIG. 1A, respectively. The catheter's structure and functioning is described with reference to these figures in the following section.

The crossing balloon catheter 100 may include a catheter shaft 102 having a proximal end 104, a distal end 106, a proximal end portion 108, and a distal end portion 110. The catheter 100 may further include a hub assembly 112 secured to the shaft's proximal end 104, an inflatable balloon 114 secured to the shaft's distal end 106, and a stiffening tube 116 positioned over the inflatable balloon 114 and the distal end portion 110 of the catheter shaft 102.

The catheter shaft 102 may include a central guidewire lumen 202 extending from its distal end 106 to its proximal end 104, or a portion thereof. A guidewire 204 may be inserted through this lumen 202 and thus the catheter 100 may be advanced over the guidewire 204 through a vasculature. The shaft 102 may have any cross-sectional shape, such as circular, rhombic, rectangular, oval, semicircular, or any other suitable shape. Moreover, the shaft's diameter may also depend on the dimensions of the vasculature. For example, the diameter of the shaft 102 may be approximately equal to 3F or 4F in some embodiments, allowing the catheter 100 to easily glide in the vasculature without damaging the vessel walls. Further, the catheter shaft 102 may have a uniform cross-section or diameter from its distal end 106 to proximal end 104. Alternatively, the cross-section and diameter may vary through its length.

Because the catheter shaft 102 may remain within a patient's body for extended periods, the device may be made of non-allergic or biocompatible material. Such materials include polyamide, polyether block amide (PEBA), silicones, polyvinyl chloride (PVC), and nylon. It will be understood that any other suitable material may just as easily be used. In some instances, coatings useful to the function of the catheter, such as lubricious coatings, may be applied to the catheter shaft.

To allow easy insertion of the catheter shaft 102 in the vasculature, and the guidewire 204 in the lumen 202, the inner and outer surface of the catheter shaft 102 may include a lubricious coating or lining such as high-density polyethylene (HDPE) or polytetrafluoroethylene (PTFE). Moreover, depending upon the particular implementation and intended use, the catheter shaft 102 can be rigid along its entire length, flexible along a portion of its length, or configured for flexure at only certain specified locations. For example, its distal end portion 110 may be more flexible that the rest of the shaft length as the distal end portion 110 of the catheter shaft 102 may need to guide the shaft through a tortuous path to the occlusion.

Moreover, certain radiopaque markers or bands may be placed along the length of the shaft. For example, one marker may be on the distal end 106 of the shaft, and/or one or more marker bands may be placed equidistant from each other along the length of the shaft, or otherwise arranged along the catheter shaft 102. Additionally or alternatively, the catheter shaft, or portions thereof, may be made of a radiopaque material. Using a suitable imaging device, such as a fluoroscope, operators may know the exact position of the catheter 100 with respect to the patient's vasculature. Moreover, visual indicia such as a marker 117 may be placed just proximal of the stiffening tube 116 when the stiffening tube is in the first position (i.e., positioned across the balloon 114). Observing this marker, operators may know whether the catheter 100 is in the first position or the second position during the medical procedure.

The catheter shaft 102 may include an expandable member, such as an inflatable balloon 114, disposed at the distal end of the catheter shaft 102. The inflatable balloon 114 may be coupled to the distal end portion 110 of the elongate shaft 102 proximate the distal end 106. The balloon 114 may be made from typical angioplasty balloon materials including polymers such as polyethylene terephthalate (PET), polytetrafluoroethylene (PTFE), ethylene tetrafluoroethylene (ETFE), polybutylene terephthalate (PBT), polyurethane, polyvinylchloride (PVC), polyether-ester, polyester, polyamide, elastomeric polyamides, polyether block amide (PEBA), as well as other suitable materials, or mixtures, combinations, copolymers thereof, polymer/metal composites, and the like.

In other embodiments, the expandable member may be an expandable basket, cage, scaffold, or other mechanically expandable structure. In some embodiments, the expandable member may be formed of a shape memory alloy such as nitinol, stainless steel, or other metal alloy, or a polymeric material, if desired. In these instances, the expandable member may be a collapsible or self-expandable basket having several legs longitudinally extending along the length of the distal end portion. On actuation, the central portion of each leg may spring radially into an expanded configuration. Suitable actuation mechanisms such as levers, electronic switches, or wires may be introduced in the hub assembly 112 to actuate the expandable member, when desired, or the expandable member may be automatically expandable once unconstrained. Other collapsible or self-expandable structures formed of shape memory alloys, shape memory polymers, or other materials may also be contemplated without departing from the scope of the present disclosure.

In the illustrated embodiment, the balloon 114 may be a membrane, which may switch between a deflated and inflated state using expansion agents such as fluids, having a particular density. In the deflated state, the balloon 114 may be folded and wrapped around the distal portion of the shaft, as shown in FIG. 2. Once the balloon 114 is positioned in the occlusion, the expansion agent may be introduced in the balloon through the inflation lumen 306, inflating it. The inflated balloon 114 may exert a radial force on the occlusion, increasing the vessel diameter at the occlusion site and allowing unrestricted passage of blood through the occlusion.

FIG. 2, which is a cross-section taken along line 2-2' of FIG. 1A, illustrates one such balloon 114 in the deflated state positioned in the stiffening tube 116. Here, the balloon 114 may be coupled to the distal portion of the shaft 102 by means of an adhesive, or other bonding means such as RF signal, laser, or other thermal bonding. The interior of the balloon 114 may be in fluid communication with the inflation lumen 306 such that expansion agents may be introduced through the inflation lumen 306 of the catheter shaft 102 to inflate the balloon 114.

FIG. 3 is a cross-section taken along line 3-3' of FIG. 1A. Here, the shaft 102 may include an outer tubular member 302, which may be coaxially disposed about an inner tubular member 304 to define an annular inflation lumen 306 between the members over a substantial portion of the length of the shaft. The inflation lumen 306 may extend from a port in the hub assembly 112 to the balloon 114. In some embodiments, the outer tubular member 302 may have an outer diameter ranging from about 0.030 inches to about 0.050 inches with a wall thickness ranging from about 0.0028 inches to about 0.006 inches in some instances. In one embodiment, the outer tubular member 302 may have an outer diameter of about 0.045 inches, an inner diameter of about 0.035 inches, and a wall thickness of about 0.005 inches. Materials used to form the outer tubular member 302 may vary to achieve the stiffness desired for the shaft 102. Nylon and polyamides are examples of suitable polymers for outer tubular members 302.

The inner tubular member 304 may define the guidewire lumen 202, which provides a passage for the guidewire 204 therethrough. Moreover, the inner tubular member 304 may be made of the same material as the outer tubular member 302, or a different material, and may be configured such that when placed within the outer tubular member 302, the gap left between the two tubular members defines the annular inflation lumen 306. The inner diameter of the inner tubular member 304 may be sized to allow a standard guidewire 204 to pass through as the catheter shaft 102 is advanced over the guidewire 204. Moreover, the wall thickness and/or diameters of the tubular members may depend on the required stiffness and on the ability of the members to resist kink formations along their lengths.

To couple the balloon 114 to this tubular configuration, a proximal portion of the balloon 114 may be fixed to the outer tubular member 302 and a distal portion may be fixed to the inner tubular member 304. This particular arrangement may allow the expandable balloon 114 to be in fluid communication with the annular inflation lumen 306. The inflatable balloon 114 and techniques of coupling the balloon 114 to a distal portion of the shaft 102 are commonly known in the art and will not be described here further.

Referring back to FIGS. 1A and 1B, the hub assembly 112 connected to the shaft's proximal end 104 may include multiple ports 118 for inserting medical instruments such as guidewires in the guidewire lumen 202, or inflation agents such as fluids in the inflation lumen 306. The hub assembly 112 may be permanently or temporarily attached to the proximal end 104 of the catheter shaft 102. For permanent attachment, the hub 112 may be glued, welded, or molded with the catheter shaft 102. For temporary attachment, the hub 112 and the shaft's proximal end 104 may include engaging elements such as protrusions, screw threads, or luer-lock elements. These elements may engage each other to form a connection. In some embodiments, the hub assembly 112 may include actuation means to actuate the expandable member in instances where the expandable member is mechanically expandable, to guide or deflect the distal end portion 110 of the catheter 100, and/or guide the guidewire 204. Further, the hub assembly 112 may include features to allow an operator to grasp the catheter 100 comfortably. For example, the hub assembly 112 may include a handle portion, grooves adapted for an operator's fingers, etc.

The stiffening tube 116, as previously mentioned, may surround the catheter shaft 102, and be coupled to the shaft 102 such that it is translatable along the catheter shaft 102 from a first position (also referred to as a crossing position) to a second position (also referred to as a deployed position). FIG. 1A illustrates the stiffening tube 116 in the crossing position and FIG. 1B illustrates the tube in the deployed position. In the crossing position, the inflatable balloon 114 may be within the stiffening tube 116; and in the deployed position, the inflatable balloon 114 may be exposed from the stiffening tube 116. The stiffening tube 116 may be placed in the crossing position to provide additional stiffness to the shaft's distal end portion 110 to cross an occlusion. Further, the stiffening tube 116 may be withdrawn to be placed in the deployed position once the occlusion is crossed and the operator is ready to inflate the balloon 114.

In some instances in which the inflatable balloon 114 may include a coating, such as a lubricious coating or a drug eluting coating, the stiffening tube 116 may provide a cover or protective barrier over the inflatable balloon 114. For instance, in instances in which the inflatable balloon 114 includes a lubricious coating, the stiffening tube 116, overlaying the balloon 114, may prevent "watermelon seeding" (i.e., slipping of the balloon 114 in a stenosis). In instances in which the inflatable balloon 114 includes a drug coating, the stiffening tube 116 may protect the coating from inadvertent or premature exposure, and/or the stiffening tube 116 may prevent the drug from washing off of the inflatable balloon 114 or eluding from a polymer carrier before the balloon 114 reaches the site of the stenosis.

To translate the stiffening tube 116 between these two positions over the shaft 102, the length of the stiffening tube 116 may be shorter than the length of the shaft 102. In one embodiment, the stiffening tube 116 may extend along about 70% or more, about 80% or more, or about 90% or more of the length of the shaft 102. It will be understood, however, that the length of the stiffening tube 116 may also depend on the length of the inflatable balloon 114. For example, the stiffening tube 116 may be sized to be sufficiently shorter than the shaft 102 so that when the stiffening tube 116 is pulled proximally toward the proximal end 104 of the shaft, the balloon 114 may be fully exposed at the distal portion of the shaft. In other words, the stiffening tube 116 may be permitted to axially translate along the catheter shaft 102 a sufficient distance to fully expose the balloon 114.

Moreover, the stiffening tube 116 and the catheter shaft 102 may be dimensioned such that the proximal portion 108 of the catheter shaft 102 and the stiffening tube 116 may remain exterior to a patient's body, while the balloon 114 is placed in the occlusion. This way, an operator may hold the proximal end of the stiffening tube 116 to translate it between the crossing and deployed positions after navigating the distal end 106 to a location in the vasculature proximate an occlusion. To ease an operator's grasp of the proximal end of the stiffening tube 116, the proximal end may flare outwards. The flare also ensures that the stiffening tube 116 does not inadvertently slip inside a patient's vasculature during translation. In other embodiments, the proximal end of the stiffening tube 116 may include other grasping means, such as hooks, handles, or loops. Alternatively, other actuation means including electronic means such as switches or mechanical means such as levers, or wires may be present on the hub 112 to translate the stiffening tube 116.

In other instances, the stiffening tube 116 may include a hub at a proximal end of the stiffening tube 116 configured to engage the hub 112 at the proximal end of the catheter shaft 112. For example, the hub of the stiffening tube 116 may include a threaded connector for threadably engaging a threaded connector of the hub 112. Additionally or alternatively, the proximal end of the stiffening tube 116 may include a hermetic seal or hemostasis valve to prevent blood from leaking between the stiffening tube 116 and the catheter shaft 102.

In some embodiments, the stiffening tube 116 may be configured to be removable from the catheter shaft 102 while the catheter shaft 102 remains in place in the vasculature. For example, in some instances, the stiffening tube 116 may include a preferential score line, weakened area, perforated line, or other feature along which portions of the stiffening tube 116 may be separated to permit the stiffening tube 116 to be completely removed from the catheter shaft 102 in situ.

To enable smooth translation, a lubricious coating may be applied to the inner surface of the stiffening tube 116. Other low friction translation means may also be considered. For example, in some embodiments, the inner surface may include guide rails and the outer surface of the shaft 102 may include longitudinal protrusions that slide into the guide rails for movement, or vise versa.

The wall thickness and/or diameter of the stiffening tube 116 may depend on the desired application. For example, the stiffening tube may be rigid enough to penetrate soft plague, hard plaque, or calcifications. In some embodiments, the wall thickness of the stiffening tube 116 may be approximately in the range of 0.004 inches to 0.008 inches, or about 0.006 inches. Moreover, the stiffening tube 116 may closely surround the catheter shaft 102 to stiffen the shaft 102 such that the stiffening tube 116 frictionally engages the catheter shaft 102 as the stiffening tube 116 is translated along the catheter shaft 102. For instance, in some embodiments, the inner diameter of the stiffening tube 116 may be about 0.04 inches, or about 0.05 inches and the outer diameter of the catheter shaft 102 may be about 0.05 inches or about 0.06 inches. The stiffening tube 116 may be dimensioned such that the difference in inner diameter of the stiffening tube 116 and the outer diameter of the catheter shaft 102 is less than 0.003 inches or less than 0.002 inches in some instances. Accordingly, the gap between the inner diameter of the stiffening tube 116 and the outer diameter of the catheter shaft 102 may be 0.0015 inches or less, or 0.001 inches or less. For instance, in one embodiment, the inner diameter of the stiffening tube 116 may be about 0.047 inches while the outer diameter of the catheter shaft 102 may be about 0.045 inches. The inner diameter of the stiffening tube 116 may be dimensioned to accommodate the folded balloon 114 therein.

Suitable materials to form the stiffening tube 116 may include Teflon, polyethylene, nylon, polyesters, polyoxyethylenes, or polyether ether ketones (PEEK). Other lubricious or biocompatible materials such as other known polymer thermoplastics may also be considered without departing from the scope of the present disclosure.

In some instances, the integrated crossing balloon catheter 100 may be inserted in the vasculature of a patient and the distal portion of the catheter 100 urged distally until it reaches an impassable occlusion, such as a chronic total occlusion (CTO). In such an instance, the catheter 100 may be configured to penetrate or pass through the occlusion with the stiffening tube 116 in the crossing position (i.e., with the stiffening tube 116 extending over the balloon 114). Subsequently, when the crossing catheter 100 has crossed the occlusion or the balloon 114 is otherwise positioned across the occlusion, the stiffening tube 116 may be partially retracted such that the balloon 114 is exposed. In this manner, the occlusion may be crossed and the balloon 114 may be placed in the occlusion to dilate the occlusion without the need of exchanging any medical devices.

In some instances, in the crossing position, the balloon 114 may be partially inflated within the stiffening tube 116 to increase the rigidity of the catheter 100 while penetrating through a tough occlusion. In some instances, the stiffening tube 116 may be sufficiently rigid, and thus not radially expand when the balloon 114 is inflated therein.

In other instances, the stiffening tube 116 may be configured to include an expandable region surrounding the balloon 114, which may be readily expandable when subjected to a radially outward force generated by inflating the balloon 114 against the interior wall of the expandable portion of the stiffening tube 116. FIGS. 4A-4B illustrate one such embodiment. More particularly, FIG. 4A illustrates the catheter with a deflated balloon 114 positioned within an expandable portion 402 of the stiffening tube 116 and FIG. 4B illustrates the catheter with the balloon 114 inflated to radially expand the expandable portion 402. The expandable balloon 114 may be coupled between the distal end of the inner tubular member 304 and the distal end of the outer tubular member 302 with a well-defined inflation lumen 306 therebetween. In this embodiment, the distal portion of the stiffening tube 116 may include an expandable portion 402, which may be readily expanded when the balloon 114 is inflated therein. Particularly, a distal portion of the stiffening tube 116, which may or may not exclude the distal terminal end of the stiffening tube 116, may be expandable. Thus, when the balloon 114 is inflated, the expandable portion 402 may also expand. The expandable portion 402 may be formed of any desired material, such as a distensible polymeric material, including elastomeric polymers, rubber, latex, etc. The degree of expansion may depend on the rigidity of the expandable portion 402, pressure applied by the balloon 114, and/or other such factors. In such embodiments, the balloon 114 may be inflated within the stiffening tube 116, even after the occlusion is crossed and the balloon 114 is positioned across the occlusion within the stiffening tube 116. Accordingly, the occlusion may be dilated or expanded by the combined force of the stiffening tube 116 and the inflated balloon 114 therein, expanding radially outward against the occlusion.

FIGS. 5A and 5B illustrate another exemplary embodiment of the crossing balloon catheter 100 in which the stiffening tube 116 includes an expandable region formed in the stiffening tube 116. For example, the stiffening tube 116 may include one or more, or a plurality of slots 502 formed through the wall of the stiffening tube 116. FIG. 5A illustrates the distal portion of the stiffening tube 116 with a deflated balloon 114 and FIG. 5B illustrates the stiffening tube 116 with the balloon 114 inflated therein. Here, the expandable portion 402 includes longitudinal slots 502 defining longitudinal struts 410 therebetween. When the balloon 114 is deflated, the diameter of this expandable portion 402 may be equal to the diameter of the remaining portion of the tube 116. When the balloon 114, however, is inflated, the force exerted by the balloon 114 may widen the longitudinal slots, expanding the longitudinal struts 410 radially outward, and thus enlarging the expandable portion 402. The degree of slot 502 expansion and strut 410 deflection may depend on the proximity of the stiffening tube 116 to the balloon 114, the degree of balloon 114 expansion, and/or the rigidity of the expandable material forming the struts 410.

In this embodiment, the stiffening tube 116 may function as a scoring catheter. When the balloon 114 inflates, the struts 410 may be expanded against the occlusion to score the plaque, dilating the occlusion further. Scoring may be helpful in lesions where catheter delivery may be difficult, balloon 114 slippage may occur, and/or very high pressures may be required to dilate the lesions.

FIGS. 6A and 6B also illustrate another embodiment of the expandable stiffening tube 116 including an expandable region. Here, the distal portion may include helical slots 602 that help the stiffening tube 116 to expand under pressure from an inflating balloon 114 within the expandable region. Thus, when the balloon 114 is inflated within the expandable portion 402, the expandable portion 402 may be radially expanded against an occlusion to score the plaque and/or dilate the occlusion. Once the plaque is sufficiently scored and/or dilated, the balloon 114 may be deflated, the expandable portion 402 may return to its normal size. If desired, the stiffening tube 116 may then be retracted to deploy the balloon 114 without the stiffening tube 116, and further dilation may be performed with the exposed balloon 114.

In the expandable configurations described previously with reference to FIGS. 4A-4B, 5A-5B, and 6A-6B, in some instances the expandable portion 402 may be formed of a different material than the remaining portion of the stiffening tube 116. For example, the expandable portion 402 may be formed of shape-memory alloys such as nitinol, or shape memory polymers in some instances. In other embodiments, polymeric materials, such as elastomers, or synthetic elastics may be used. Further, any suitable biocompatible expandable materials widely known in the art may be used without departing from the scope of the present disclosure. In another embodiment, the complete stiffening tube 116 may be formed of an expandable material.

FIGS. 4A-4B, 5A-5B, and 6A-6B illustrate a few exemplary expandable configurations of the stiffening tube 116. It will be understood, however, that multiple other expandable configurations are possible. For example, the expandable portion 402 may include lateral slots or cutouts of any other shape without departing from the scope of the present disclosure.

Figure 7A:
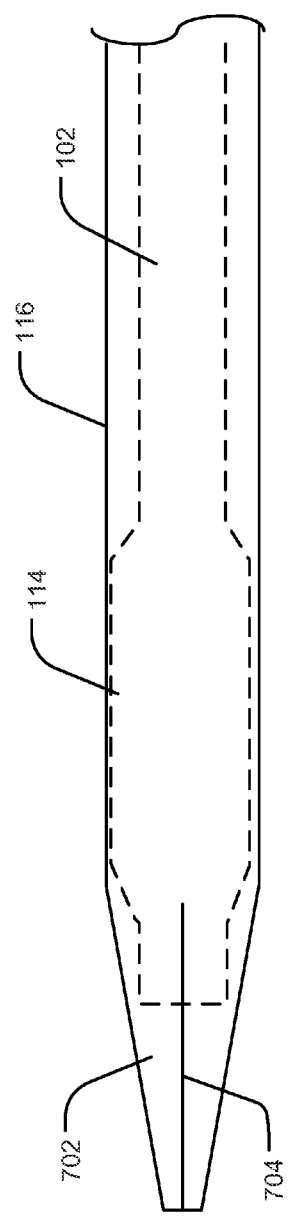
FIGS. 7A and 7B are illustrative diagrams of an exemplary distal portion of an alternative embodiment of the crossing balloon catheter in a first position and second position, respectively.
Figure 7B:
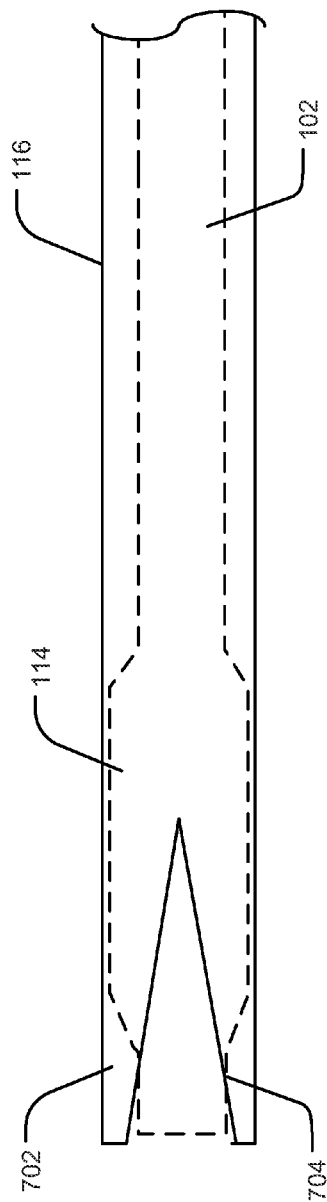

FIGS. 7A and 7B illustrate another exemplary embodiment of the crossing balloon catheter 100. FIG. 7A illustrates the distal portion of the stiffening tube 116 in the crossing position and FIG. 7B illustrates the distal portion of the stiffening tube 116 as the balloon 114 is being deployed out of the distal end of the stiffening tube 116 toward the deployed position. Here, the distal end of the stiffening tube 116 may include a tapered portion 702 to facilitate passing the catheter 100 through an occlusion. For example, the tapered tip 702 may increase the ability of the stiffening tube 116 to pierce or penetrate through an occlusion. As the tapered portion 702 may narrow to a diameter as small as the shaft 102 or even smaller, the tapered portion 702 may extend beyond the distal end 106 of the shaft 102 and the inflatable balloon 114.

Once an occlusion is crossed with the crossing catheter 100, the stiffening tube 116 may be refracted to expose the balloon 114. To facilitate retracting the stiffening tube 116 proximally, the tapered portion 702 may include one or more slits or slots 704 that enable the tapered end to expand radially when the stiffening tube 116 is pulled proximally over the inflatable balloon 114 and/or when the balloon 114 is urged distally. FIGS. 7A and 7B illustrate one slot 704, it will be understood that the tapered portion 702 may include multiple slots 704 circumferentially arranged around the tapered portion 702 in some instances.

Moreover, the tapered portion 702 may expand automatically as a result of the force exerted by the catheter shaft 102 on the tapered portion 702, or externally by an activation mechanism.

Exemplary Methods

FIGS. 8A-8H illustrate various aspects of crossing an occlusion in a vessel lumen using the crossing catheter 100. It will be understood that these aspects are merely exemplary and any of the described aspects may be modified, combined with one or more other aspects, or deleted without departing from the scope of the present disclosure. Moreover, any suitable steps to cross an occlusion may be added to any combination of aspects described herein.

As shown in FIG. 8A, during a medical procedure, such as an angioplasty procedure, a flexible guidewire 204 may be inserted in a patient's vasculature 802 from a percutaneous opening or incision. The guidewire 204 may be urged distally until it reaches an occlusion 804. In some instances, the guidewire 204 may be unable to cross the occlusion 804. For example, in some instances the guidewire 204 may lack sufficient stiffness/rigidity to advance unaided through the occlusion 804. Accordingly, aspects of the crossing catheter 100 may be utilized to facilitate crossing the occlusion 804. For example, as shown in FIG. 8B, the integrated crossing catheter 100 may be guided over the guidewire 204 to the occlusion 804.

When the crossing catheter 100 reaches the occlusion 804, in some instances the operator may try crossing the occlusion 804 with just the guidewire 204, as shown in FIG. 8C, using the crossing catheter 100 to support the guidewire 204 proximal of the occlusion 804. With the guidewire 204 now supported by the catheter 100, the guidewire 204 may be able to exert more force on the occlusion 804. In some instances, the guidewire 204 may be able to cross the occlusion 804 with this added support; for example, in cases where the occlusion is soft. In other cases, however, the guidewire 204, alone, may not be sufficient to cross the occlusion 804.

The operator may attempt to cross the occlusion 804 with the crossing catheter 100 in combination with the guidewire 204 previously positioned through the occlusion 804, or without the guidewire 204 previously positioned through the occlusion 804. For example, as shown in FIG. 8D, in some instances, the catheter shaft 102 and balloon 114 may be advanced distally of the stiffening tube 116 to cross the occlusion 804 while the stiffening tube 116 may remain proximal of the occlusion 804. Thus, the deflated balloon 114 may be positioned across the occlusion 804 while uncovered by the stiffening tube 116. In other instances, the operator may attempt to cross the occlusion 804 with the stiffening tube 116 in the crossing position, as shown in FIG. 8E (i.e., with the stiffening tube 116 positioned over the balloon 114). This arrangement may be implemented, for example, to cross hard and calcified occlusions in some instances. In some instances, the balloon 114 may be inflated (at least partially inflated) within the stiffening tube 116 to provide further rigid support between the stiffening tube 116 and the catheter shaft 102 while crossing the occlusion 804.

Once the balloon 114 of the crossing catheter 100 has been advanced across the occlusion 804, the balloon 114 may be inflated to dilate the occlusion 804. For example, as shown in FIG. 8G, the balloon 114 may be inflated with the stiffening tube 116 retracted proximally to the deployed position. Thus, inflation of the balloon 114 may exert a radial force on the occlusion 804 to dilate the occlusion 804. In other instances, such as shown in FIG. 8F, the balloon 114 may be inflated within the stiffening tube 116 to dilate the occlusion 804, urging the expandable portion 402 of the stiffening tube against the occlusion 804 to exert a radial force on the occlusion 804 and/or score the occlusion 804.

As stated previously, it will be understood that additional or alternative steps may be implemented to cross the occlusion 804, as desired. For example, if the first guidewire 204 was unable to cross the occlusion 804, the operator may attempt to cross the occlusion 804 with a stiffer guidewire before attempting to cross the occlusion 804 with the catheter 100. For example, as shown in FIG. 8H, the first guidewire 204 may be withdrawn and a stiffer guidewire 810 may be advanced through the catheter 100 to cross the occlusion 804.

Some embodiments of the present disclosure may be used in any medical or non-medical procedure, including any medical procedure where draining visceral fluid is desired. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, and departure in form and detail may be made without departing from the scope and spirit of the present disclosure as described in the following claims.

What is claimed is:

1. An integrated crossing balloon catheter comprising: a catheter shaft having a proximal end, a distal end, a proximal end portion proximate the proximal end, and a distal end portion proximate the distal end; a hub assembly secured to the proximal end of the catheter shaft; an inflatable balloon secured to the distal end of the catheter shaft; and a stiffening tube positioned over the inflatable balloon and the distal end portion of the catheter shaft, the stiffening tube configured to be advanced through a vasculature with the catheter shaft as a unit; wherein the stiffening tube is translatable along the catheter shaft within the vasculature from a first position in which a distal end of the inflatable balloon is within the stiffening tube to a second position in which a proximal end of the inflatable balloon is distal of the stiffening tube, wherein the stiffening tube includes an expandable region surrounding the inflatable balloon, wherein the expandable region includes a distensible material configured to expand radially outward when the inflatable balloon is inflated within the expandable region.

2. The integrated crossing balloon catheter of claim 1, wherein the catheter shaft has a length measured from the inflatable balloon to the hub assembly, and the stiffening tube has a length measured from a distal end of the stiffening tube to a proximal end of the stiffening tube, wherein the length of the stiffening tube is less than the length of the catheter shaft.

3. The integrated crossing balloon catheter of claim 2, wherein the stiffening tube extends along 70% or more of the length of the catheter shaft.

4. The integrated crossing balloon catheter of claim 2, wherein the stiffening tube is dimensioned such that the proximal end of the stiffening tube remains exterior of a patient while the balloon is positioned proximate a target site within a vessel lumen throughout a medical procedure.

5. The integrated crossing balloon catheter of claim 2, wherein the proximal end of the stiffening tube is flared outward to be grasped by a physician in order to manipulate the stiffening tube.

6. The integrated crossing balloon catheter of claim 2, wherein the inflatable balloon has a length, and the stiffening tube is translatable relative to the catheter shaft over a distance at least as long as the length of the inflatable balloon.

7. The integrated crossing balloon catheter of claim 1, wherein the stiffening tube frictionally engages the catheter shaft as the stiffening tube is translated along the catheter shaft.

8. The integrated crossing balloon catheter of claim 7, wherein the catheter shaft has an outer diameter and the stiffening tube has an inner diameter, wherein the difference between the outer diameter of the catheter shaft and the inner diameter of the stiffening tube is 0.002 inches or less.

9. The integrated crossing balloon catheter of claim 1, wherein the catheter shaft includes visual indicia located proximate a proximal end of the stiffening tube when the stiffening tube is at the first position to indicate the stiffening tube is positioned over the inflatable balloon.

10. An integrated crossing balloon catheter system comprising: a catheter including an elongate shaft extending from a hub assembly at a proximal end of the catheter to an inflatable balloon at a distal end of the catheter, the catheter including an inflation lumen extending through the elongate shaft from the hub assembly to the inflatable balloon for delivering inflation fluid to the inflatable balloon; a stiffening tube having a proximal end, a distal end and a length measured from the proximal end to the distal end, the stiffening tube surrounding the elongate shaft and in intimate contact with an outer surface of the elongate shaft along a majority of the length of the elongate shaft, the stiffening tube configured to be advanced through a vasculature with the catheter as a unit; wherein the stiffening tube is translatable along the elongate shaft within the vasculature from a first position in which a distal end of the stiffening tube is positioned distal of the inflatable balloon to a second position in which the distal end of the stiffening tube is positioned proximal of the inflatable balloon, wherein the stiffening tube includes an expandable region surrounding the inflatable balloon, wherein the expandable region includes a distensible material configured to expand radially outward when the inflatable balloon is inflated within the expandable region.

11. The system of claim 10, wherein the elongate shaft of the catheter has a length measured from the inflatable balloon to the hub assembly, wherein the length of the elongate shaft is greater than the length of the stiffening tube.

12. The system of claim 11, wherein the length of the stiffening tube is 70% or more of the length of the elongate shaft of the catheter.

13. The system of claim 10, wherein the stiffening tube has a tapered distal tip configured to expand from a first configuration to a second configuration, the first configuration being a low profile configuration for traversing an occlusion and the second configuration being sized to allow the inflatable balloon to be deployed through the tapered distal tip.

14. The system of claim 10, wherein the expandable region includes a plurality of slots.

15. An integrated crossing balloon catheter system comprising:
a catheter including an elongate shaft extending from a hub assembly at a proximal end of the catheter to an inflatable balloon at a distal end of the catheter, the catheter including an inflation lumen extending through the elongate shaft from the hub assembly to the inflatable balloon for delivering inflation fluid to the inflatable balloon; and
a stiffening tube having a proximal end, a distal end and a length measured from the proximal end to the distal end, the stiffening tube surrounding the elongate shaft and in intimate contact with an outer surface of the elongate shaft along a majority of the length of the elongate shaft, the stiffening tube configured to be advanced through a vasculature with the catheter as a unit;
wherein the stiffening tube includes an expandable region, excluding the distal terminal end thereof, surrounding the inflatable balloon.

16. The system of claim 15, wherein the expandable region is configured to expand from a first diameter to a second diameter upon inflating the inflatable balloon within the expandable region.

17. The system of claim 15, wherein the expandable region comprises a distensible polymeric material.

18. The system of claim 17, wherein the expandable region is readily expandable when the inflatable balloon is inflated therein.

* * * * *